United States Patent [19]

Evers et al.

[11] 4,065,408
[45] Dec. 27, 1977

[54] α-OXY(OXO) SULFIDE PERFUME AND COLOGNE COMPOSITIONS

[75] Inventors: William J. Evers, Red Bank; Howard H. Heinsohn, Jr., Hazlet, both of N.J.; Edward J. Shuster, Brooklyn, N.Y.; Frederick Louis Schmitt, Holmdel, N.J.

[73] Assignee: International Flavors & Fragrances Inc., New York, N.Y.

[21] Appl. No.: 723,534

[22] Filed: Sept. 15, 1976

[51] Int. Cl.[2] .............................................. C11B 9/00
[52] U.S. Cl. ........................... 252/522; 260/593 R; 260/609; 252/89 R; 252/108; 252/173; 252/368; 424/70; 424/73
[58] Field of Search .................... 252/522; 260/593 R

[56] References Cited

U.S. PATENT DOCUMENTS

| 2,888,487 | 5/1959 | Asinger et al. | 260/593 R |
|---|---|---|---|
| 3,773,524 | 11/1973 | Katz et al. | 260/593 R |
| 3,948,816 | 4/1976 | Helmlinger et al. | 252/522 |
| 3,950,429 | 4/1976 | Lamparsky et al. | 252/522 |
| 3,952,062 | 4/1976 | Lamparsky et al. | 260/598 |
| 3,954,843 | 5/1976 | Helmlinger et al. | 252/522 |
| 3,966,989 | 6/1976 | Pittel et al. | 252/522 |
| 3,975,311 | 8/1976 | Helmlinger et al. | 252/522 |

*Primary Examiner*—Veronica O'Keefe
*Attorney, Agent, or Firm*—Arthur L. Liberman; Franklin D. Wolffe

[57] ABSTRACT

Perfume and fragrance compositions and perfumed articles including soaps, detergents, powders as well as colognes containing α-oxy(oxo) sulfides having the structure:

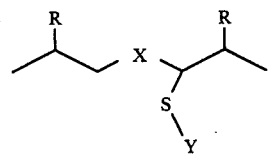

wherein R is methyl or hydrogen; X is one of

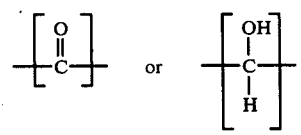

and Y is one of methyl, methallyl (having the structure:

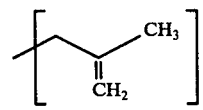

1-propyl, 2-methyl-1-propyl and acetyl which impart thereto sweet, green, floral, herbal, vegetative, basil-like, minty, melony, grapefruit, fruity and alliaceous aromas with yara, neroli and/or verdima-like nuances.

12 Claims, 22 Drawing Figures

NMR SPECTRUM FOR EXAMPLE I-B
SOLVENT: CDCL$_3$
SWEEP WIDTH: 2000Hz

I R SPECTRUM FOR EXAMPLE I(C)

IR SPECTRUM FOR EXAMPLE I(D)

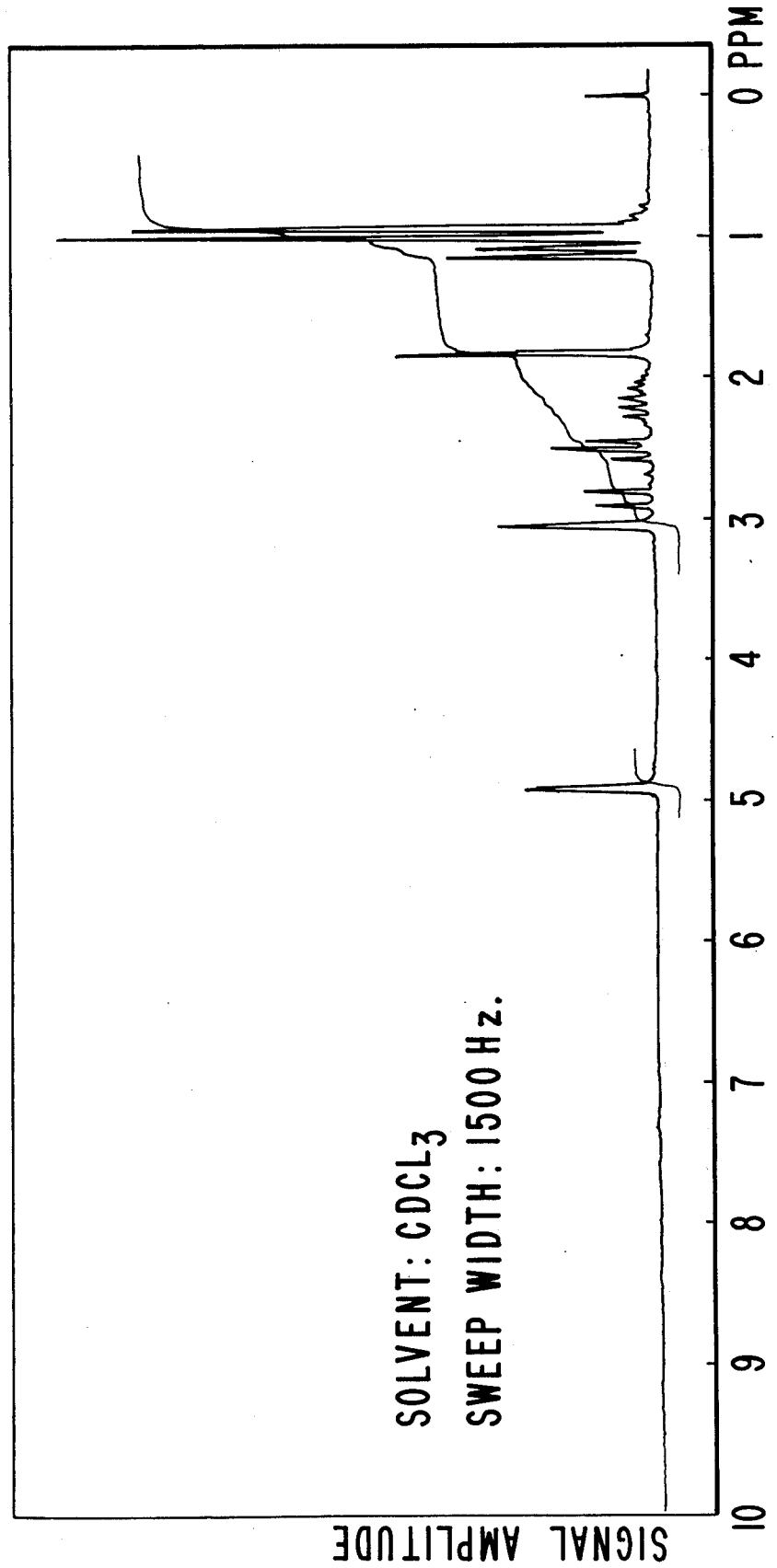

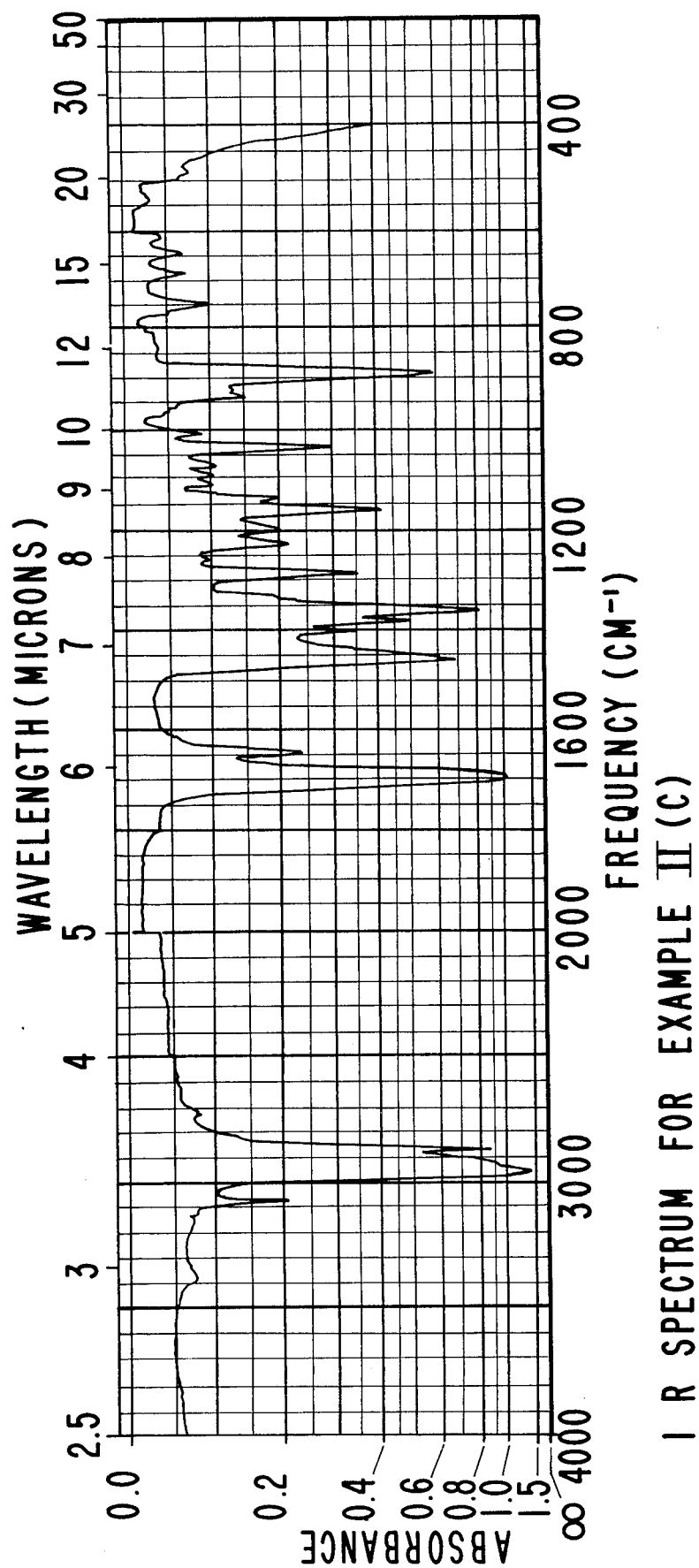

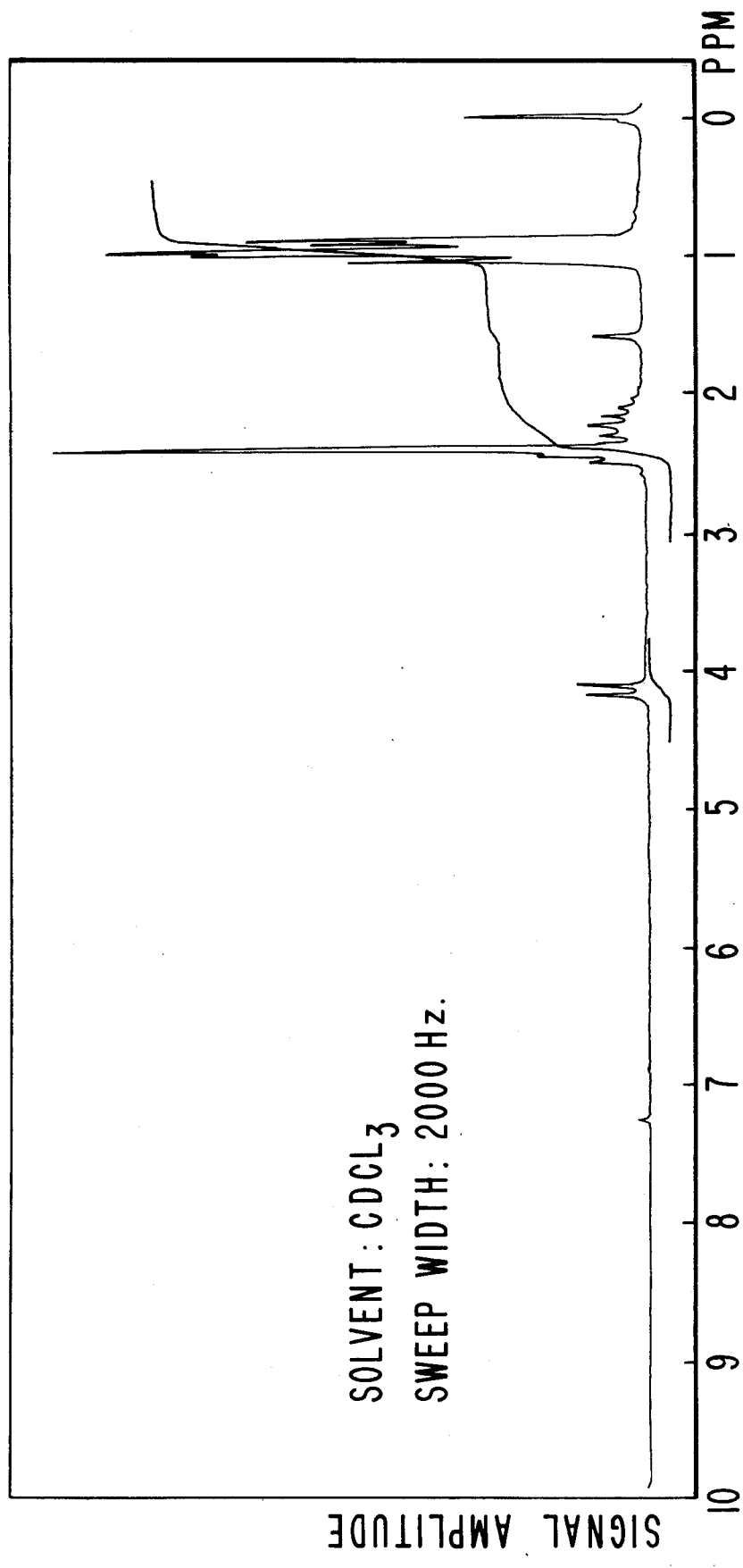

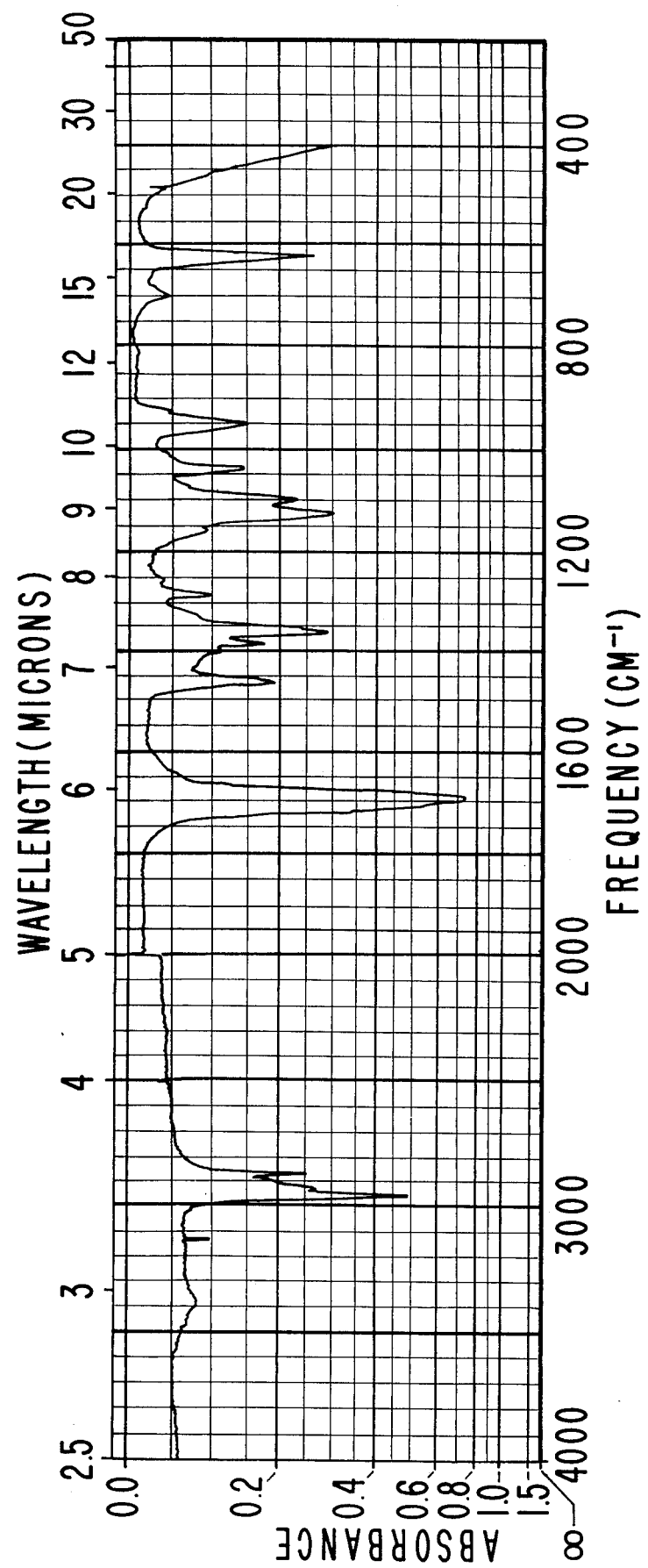

IR SPECTRUM FOR EXAMPLE III(A)

FIG.12 IR SPECTRUM FOR EXAMPLE III(B)

NMR SPECTRUM FOR EXAMPLE IV

SOLVENT: CDCL₃
SWEEP WIDTH: 2000 Hz.

IR SPECTRUM FOR EXAMPLE IV

NMR SPECTRUM FOR EXAMPLE V(A)

SOLVENT: $CDCL_3$
SWEEP WIDTH: 2000 Hz.

I R SPECTRUM FOR EXAMPLE V(A)

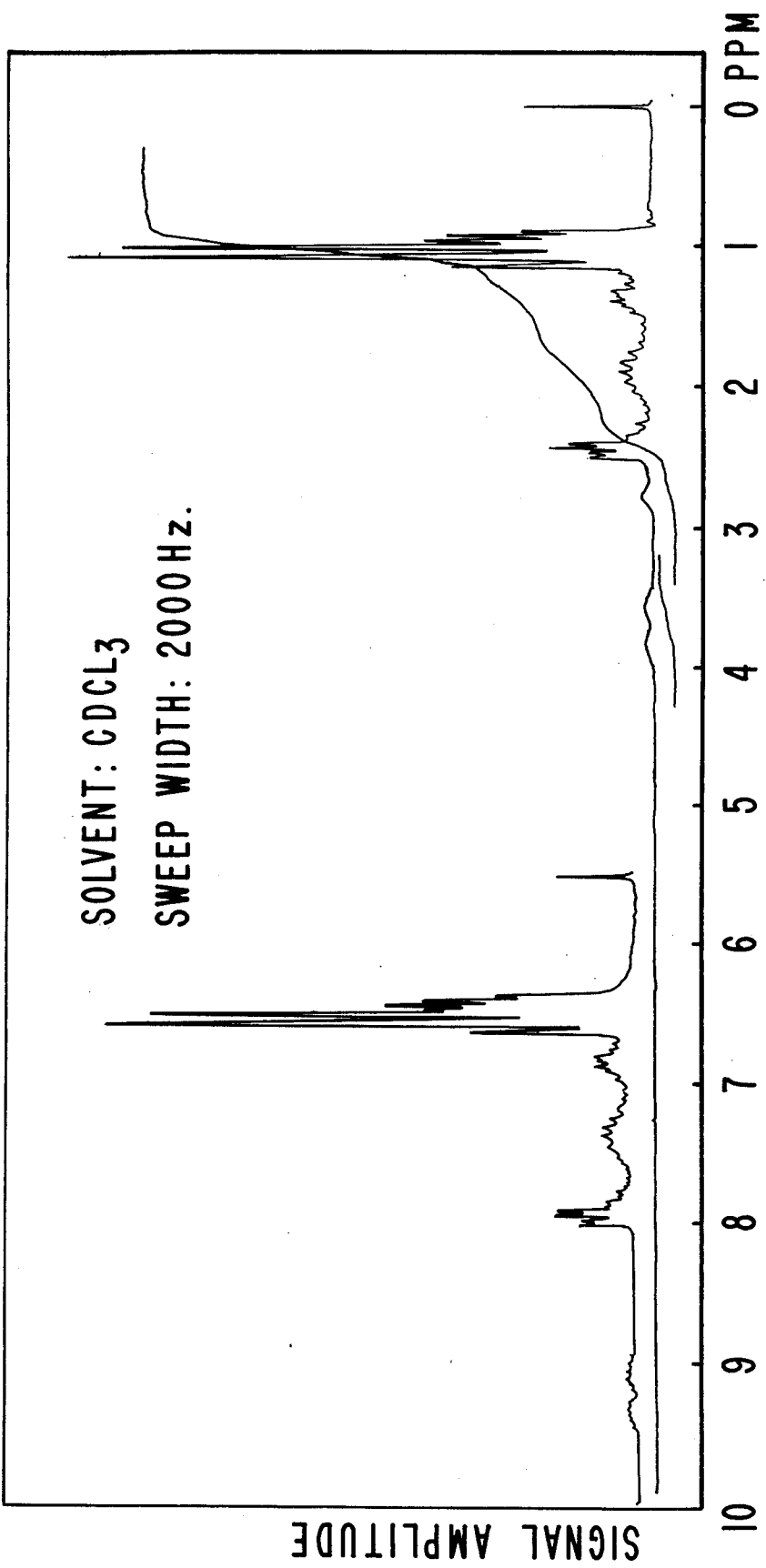
FIG.15 NMR SPECTRUM FOR EXAMPLE V(B)
SOLVENT: CDCL₃
SWEEP WIDTH: 2000 Hz.

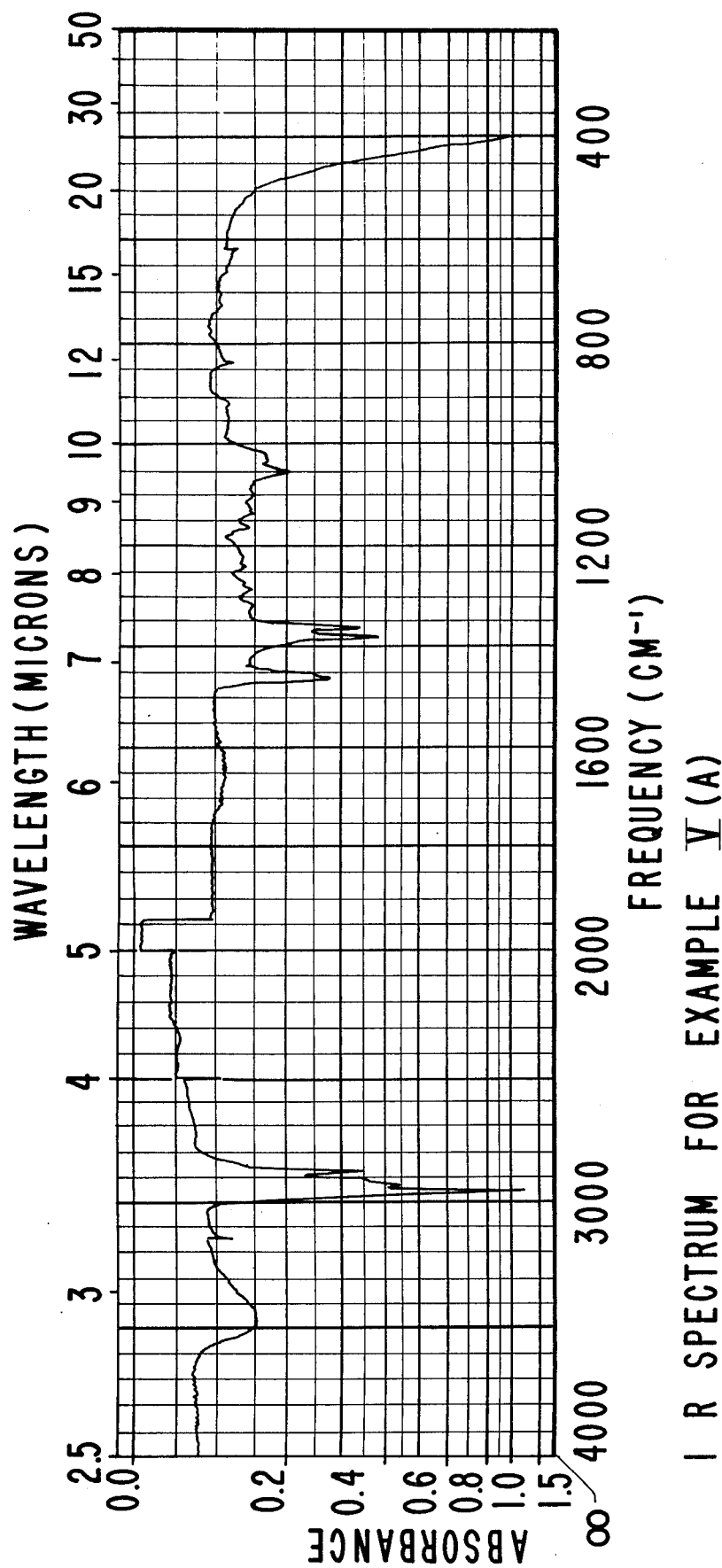

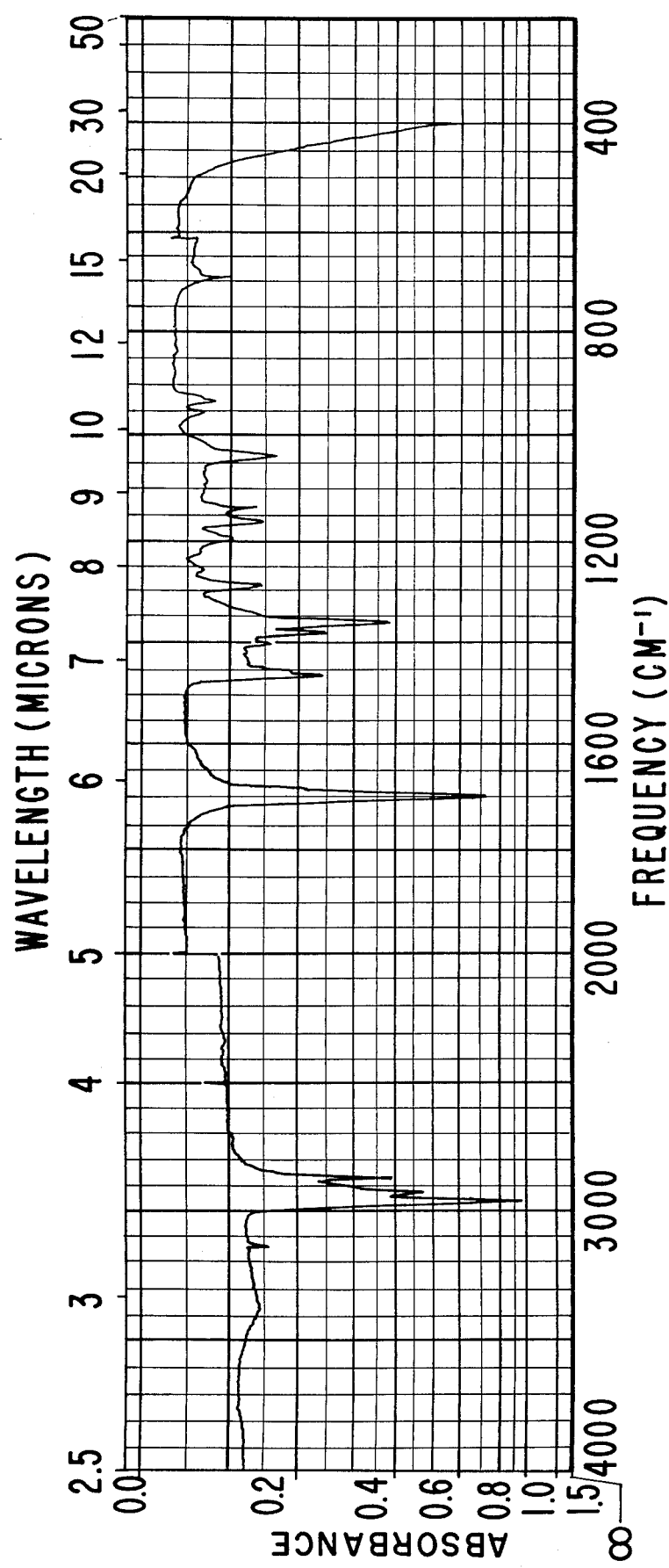

α-OXY(OXO) SULFIDE PERFUME AND COLOGNE COMPOSITIONS

BACKGROUND OF THE INVENTION

There is a continuing search for materials having desirable fragrance properties. Such materials are sought either to replace costly natural materials or to provide new fragrances or perfume types which have not heretofore been available. Especially desirable qualities for substances having interesting hyacinth fragrances, or narcisse fragrances, or violet fragrances, or oriental vetivert fragrances, or otto of rose fragrances are stability and persistance, particularly in a wide variety of perfumed articles (e.g., soaps, detergents and powders), perfume compositions and colognes, ease of manufacture and intensity of aroma.

Prior to this last decade it was the general opinion among those skilled in the art that compounds containing the mercapto or —SH moiety or substituted mercapto or —SR moiety (where R is an organic group such as alkyl or acetyl) were not desirable for use in conjunction with fragrance materials and perfumed articles such as soaps, detergents and powders. However, within the last decade such compounds have been ascertained to be highly useful in perfumery.

Thus, for example, British Pat. No. 1,423,914 and 1,423,915 issued on Feb. 4, 1976, teach that certain mercapto derivatives which are aliphatic or cycloaliphatic compounds having the formula:

$$\begin{array}{c} R^4 \\ \diagup \\ R^3 \end{array} C - CH_2 - C \begin{array}{c} X^1 \\ \diagup \\ R^1 \end{array} X^2$$

wherein X' represents a hydroxyl group or an acyloxy group, and $X^2$ represents a hydrogen atom; $R^1$, $R^2$, $R^3$ and $R^4$ may be the same or different and each represents a hydrogen atom or a univalent aliphatic hydrocarbyl group; or $R^1$ and $R^3$ or $R^4$, together with the intervening carbon atoms, constitute a cycloaliphatic ring, are useful as perfuming agents as exemplified by adding 3-methylthio-hexanol to a perfume base composition of the "Fleuri" type wherein the 3-methylthio-hexanol is said to give rise to a green, fruity aroma reminiscent of that of rhubarb.

Furthermore, for example, Canadian Pat. No. 983,050 issued on Feb. 3, 1976, teaches that 3,7-dimethyl-octa-2,6-dienyl-mercaptan (thiogeraniol) of the formula:

is used in making up a "synthetic buchu lead oil" and imparts to a lavender type composition a greener and more herbal fragrance. USSR Pat. No. 345,677 teaches that para-menthane-8-thiol-3-one is useful as a synthetic black currant flavoring for foodstuffs. This compound has the structure:

German Offenlegungschrift Pat. No. 2,316,456, published on Oct. 11, 1973 discloses the use of certain thio alcohols or their corresponding esters in perfumery and in perfumed articles, such as detergents, cosmetics and waxes. Such mercapto alcohols having the generic structure:

wherein $R_1$ is a hydrocarbon moiety having from 1 up to 7 carbon atoms and $R_2$ is one of hydrogen, methyl or ethyl.

U.S. Pat. Nos. 3,950,429 issued on Apr. 13, 1976, and 3,952,062 issued on Apr. 20, 1976, disclose certain alkylthiosubstituted oxo-terpenoids having 10 carbon atms in the terpenoid skeleton as useful in perfumery and in flavors, particularly for providing vegetable notes. The generic structure of the compounds is as follows:

wherein $R^1$ represents hydrogen or together with $R^4$ represents a C—C bond, $R^2$ represents hydrogen or together with $R^6$ represents a dimethylmethylene group, or, when $R^6$ is isopropyl, together with $R^5$ represents a C C bond, $R^3$ represents hydrogen or together with $R^6$ represents a dimethylmethylene group, $R^4$ represents hydrogen or together with $R^1$ represents a C C bond, $R^5$ represents hydrogen or, when $R^6$ signifies isopropyl, together with $R^2$ represents a C C bond, $R^6$ represents isopropyl or together with $R^2$ or with $R^3$ represents a dimethylmethylene group, $R^7$ represents methyl, X represents a C C double bond taking the place of a C C single bond, m = 0 to 2, Y represents oxo bound to a primary or secondary C-atom and Z represents mercapto or lower alkylthio located in the β-position to the carbonyl function, provided that when $R^2$, $R^3$ and $R^5$ represent hydrogen, $R^6$ represents isopropyl, $R^4$ together with $R^1$ represents a C C bond, Y is β to the carbon atom bearing the substituent $R^7$, m = o, Z is α to the carbon atom bearing the substituent $R^5$ and β to the carbon atom bearing the substituent $R^3$, then Z represents alkylthio.

However, none of the disclosure of the prior art contains a teaching to the effect that compounds having the generic structure:

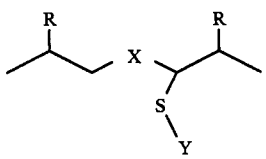

wherein R is one of methyl or hydrogen; X is one of

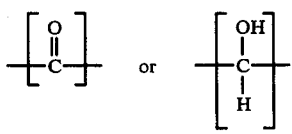

and Y is one of methyl, methallyl having the structure:

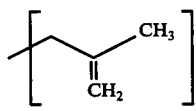

n-propyl, 2-methyl-1-propyl or acetyl, has the ability to create an intense sweet and/or green and/or floral and/or herbal and/or vegetative and/or basil-like and/or minty and/or melony and/or grapefruit and/or fruity and/or alliaceous aroma with yara and/or neroli and/or verdima nuances as is carried out using the instant invention. Furthermore, other substituted mercaptans in the prior art which are shown to be useful in perfumery and other mercaptans in the prior art which are shown to be useful in perfumery are indicated to have rhubarb-like or berry or other type floral fragrances, e.g., ionone and irone derivatives having the structure:

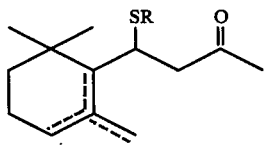

as disclosed in British Pat. No. 1,327,320, published on Aug. 22, 1973, wherein one of the dashed lines represents a double bond, and where R is hydrogen or alkyl.

Certain α-oxomercaptoalkanes are disclosed in the prior art, but their uses in perfumery, in perfumed articles or in colognes are not disclosed. Thus, U.S. Pat. No. 3,773,524, issued on Nov. 20, 1973, discloses the use of α-ketothiols of the formula:

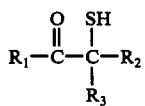

wherein $R_1$ is methyl or ethyl; and $R_2$ and $R_3$ are hydrogen, methyl or ethyl to alter the meat flavor and aroma of foodstuffs. U.S. Pat. No. 3,892,878, issued on July 1, 1975, discloses the use of certain α-hydroxymercaptoalkanes to alter the flavor of foodstuffs, for example, 2-mercapto-3-butanol used in meat flavors. The genus disclosed by U.S. Pat. No. 3,892,878 is as follows:

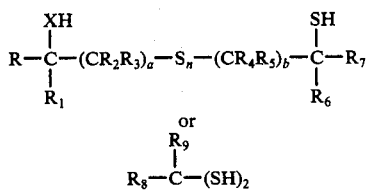

wherein X is oxygen or sulfur, $n$ is 0 or 1, $R_1$-$R_7$ are the same or different and each is hydrogen or lower alkyl of 1–4 carbon atoms, $a$ and $b$ are the same or different and each represents an integer of from 0 to 10 when $n$ is 0 and when $n$ is 1, $a$ and $b$ are the same or different annd each represents an integer of from 1 to 10. 3-mercaptoheptanone-4 is disclosed per se in U.S. Pat. No. 2,888,487, issued on May 26, 1959. 3-mercapto-2,6-dimethyl-heptan-4-one is disclosed in Chem. Abstracts 6478 (d) Vol 62, 1965 (abstract of Asinger, Diem and Schaefer, Monatsh, Chem, 95 (4-5), 1335-54 (1964). Beilstein E-IV-1 discloses 2-mercapto-2,4-dimethyl-pentan-3-on page 4039, 1-mercapto-octan-2-on at page 4040; and 1-mercapto-nonan-2-on at 4052 and 1-mercapto-undecan-2-one at page 4060.

U.S. Pat. No. 3,922,366 issued on Nov. 25, 1975, discloses the enhancemennt of foodstuffs by addition of a small but effective flavor modifying amount of a compound of the general formula:

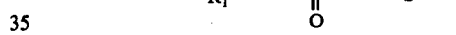

wherein $R_1$ is hydrogen or alkyl and $R_2$ is alkyl or furfuryl. The flavor nuances where are enhanced or altered are those which are found in coffee flavors and aromas.

THE INVENTION

The invention comprises novel compositions, perfumed articles and colognes containing α-oxy(oxo) sulfides having the structure:

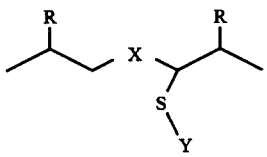

wherein X is one of:

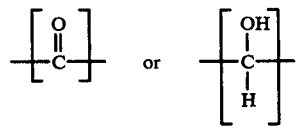

R is one of methyl or hydrogen and Y is one of methyl, methallyl having the structure:

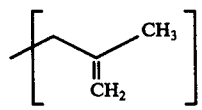

acetyl, 1-propyl or 2-methyl-1-propyl and processes for manufacturing such compositions, perfumed articles and colognes, the specific embodiments of which are described hereinafter by way of example and in accordance with which it is now preferred to practice the invention.

Briefly, the present invention provides the α-oxy(oxo) sulfides having the structure:

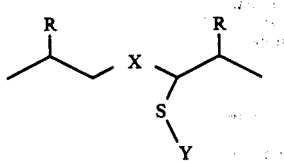

in perfume and fragrance modifying, augmenting or enhancing materials and perfumed articles including soaps, detergents and powders as well as colognes.

Such α-oxy(oxo) sulfides are obtained by reacting an alkanone with $SO_2Cl_2$ to form an α-chloroalkanone; reacting the α-chloroalkanone with an alkali metal mercpatide to form an α-substituted mercaptoalkanone which can be used for its perfumery properties; or, if desired, reacting the α-substituted mercaptoalkanone with a reducing agent such as an alkali metal borohydride in order to obtain an α-hydroxy-substituted mercaptoalkane. Thus, the aforementioned reaction sequence is illustrated as follows:

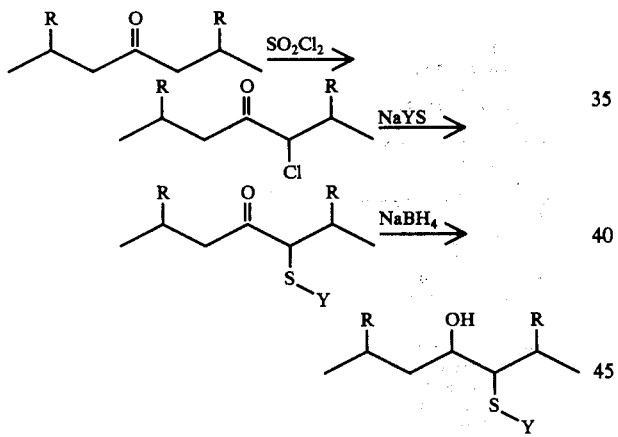

wherein Y is one of methallyl having the structure:

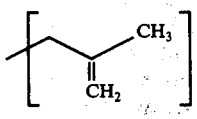

methyl 1-propyl, 2-methyl-1-propyl or acetyl; and R is one of methyl or hydrogen.

The reaction between the $SO_2Cl_2$ and the ketone preferably takes place in the absence of a solvent at a temperature of between 15° and 40° C. The $SO_2Cl_2$ is preferably added to the ketone. At the end of the reaction the reaction mass is worked up, the chlorinated ketone being distilled in vacuo.

The resulting chlorinated ketone is reacted with an alkali metal mercaptide, preferably a sodium mercaptide, preferably which is pre-prepared by reaction of sodium methylate with the appropriate mercaptan in methanol. The chlorinated ketone is preferably contained in an inert solvent, e.g., in a methanolic solution. Preferably the methanolic solution of chlorinated ketone is slowly added to the pre-prepared alkali metal mercaptide at a temperature of between 0° and 30° C; preferably between 15° and 30° C. The reaction mass is then extracted with a solvent such as methylene chloride, and the resulting extract is then worked up using evaporation and distillation techniques whereupon the α-substituted mercaptoalkanone is recovered. The resulting α-substituted mercaptoalkanone is then used "as is" for its perfumery properties; or it may be further reacted with a reducing agent such as an alkali metal borohydride, conveniently sodium borohydride. The reaction with sodium borohydrode takes place in an inert solvent such as anhydrous ethanol at a temperature of between 20° and 35° C. A solution in anhydrous ethanol of the α-substituted mercapto-alkanone is added to a solution in anhydrous ethanol of the alkali metal borohydride. The reaction is carried out over a period of time between 2 and 10 hours. At the end of the reaction the reaction mass is concentrated and is then admixed with water. The resulting mixture is then acidified to a pH of between 2 and 3 and then extracted with an inert extraction solvent such as methylene chloride. The methylene chloride extract is then dried, evaporated and the resulting α-substituted mercapto-alkanol is distilled in vacuo or isolated by GLC trapping.

Alternatively, the α-chloroketone may be reacted with an alkali metal hydrosulfide such as sodium hydrosulfide, NaHS, to form the corresponding α-mercaptoketone. The α-mercaptoketone may then be reacted with base (e.g., sodium methoxide) to form the alkali metal salt. The alkali metal salt of the α-mercaptoketone is then reacted with an alkyl or alkenyl halide (e.g., methallyl chloride) thereby forming the desired α-substituted mercaptoketoalkane which may then if desired be used as such for its organoleptic properties, or it can be reduced with the alkali metal borohydride to the corresponding α-substituted mercaptohydroxyalkane. This reaction sequence is illustrated as follows:

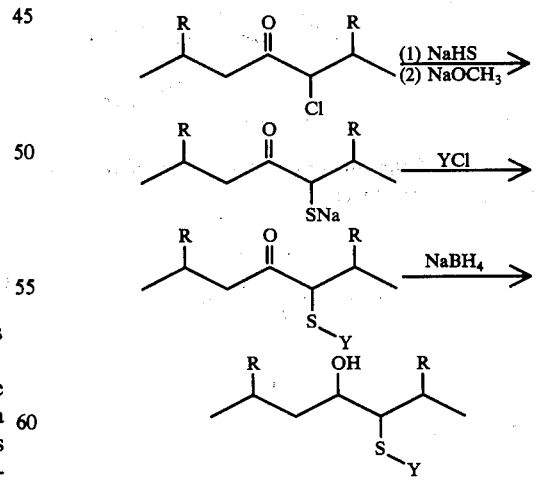

wherein R and Y are as defined above.

Specific examples of α-oxy(oxo) sulfides produced using the afore-metioned process and their perfumery properties are as follows (as set forth in Table I, below):

TABLE I

| COMPOUND | STRUCTURE | AROMA |
|---|---|---|
| 3-methylthio-4-heptanol | (structure) | At 1% in food grade ethanol, a sweet, green, floral, herbal, vegetative note. |
| 3-methylthio-4-heptanone | (structure) | At 1% in food grade ethanol a green, minty, herbaceous note with vegetative basil notes |
| 3-propylthio-4-heptanol | (structure) | Fatty, cucumber, onion (scallion, shallot) aroma with some green melon and floral nuances. |
| 3-thioacetyl-2,6-dimethyl-4-heptanone | (structure) | At 1% in food grade ethanol, a sweet, meaty, vegetable aroma with somewhat of a grapefruit topnote. |
| 3-isobutylthio-4-heptanone | (structure) | Evaluated at 1% in food grade ethanol, a meaty, onion aroma with a green, spicey and peppery nuance and an underlying Bergamot note. |
| 3-isobutylthio-2,6-dimethyl-4-heptanol | (structure) | Evaluated at 1% in food grade ethanol, a vegetable, green, horseradish, somewhat rubbery, onion-like aroma containing notes of hyacinth and narcisse. |
| 3-methylthio-2-,6-dimethyl-4-heptanone | (structure) | Evaluated at 1% in food grade ethanol, a sweet, sulfurous, slightly floral and woody aroma with a fruity and berry nuance. |
| 3-(methallylthil)-2,6-dimethyl-4-heptanone | (structure) | At 1% in ethanol, a fruity, grapefruit, somewhat floral aroma with underlying yara neroli notes and bready, vegetative nuances. |

One or more of the aforementioned α-oxy(oxo) sulfides having the structure:

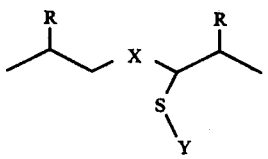

wherein X is one of:

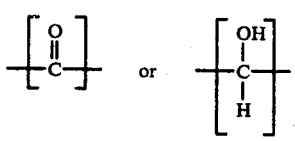

R is one of methyl or hydrogen, and Y is one of methyl, methallyl, acetyl, 1-propyl, or 2-methyl-1-propyl is an olfactory agent and can be incorporated into a wide variety of compositions each of which will be enhanced or augmented by its sweet, green, floral, herbal, vegetative, basil-like, minty, melony, grapefruit, fruity and/or alliaceous notes and/or yara, neroli and/or verdima nuances.

The α-oxy(oxo) sulfides or mixture of α-oxy(oxo) sulfides can be added to perfume compositions as pure compounds or can be added to mixtures of materials in fragrance-imparting compositions to provide a desired fragrance character to a finished perfume material. The perfume and fragrance compositions obtained according to this invention are suitable in a wide variety of perfumed articles and can also be used to enhance, modify or reinforce natural fragrance materials. It will thus be appreciated that the α-oxy(oxo) sulfide(s) of our invention is(are) useful as olfactory agent(s) and fragrance(s).

The term "perfume composition" is used herein to mean a mixture of compounds, including, for example, natural oils, synthetic oils, alcohols, aldehydes, ketones, esters, lactones, nitriles and frequently hydrocarbons which are admixed so that the combined odors of the individual components produce a pleasant or desired fragrance. Such perfume compositions usually contain (a) the main note or the "bouquet" or foundation-stone of the composition; (b) modifiers which round-off and accompany the main note; (c) fixatives which include odorous substances which lend a particular note to the perfume throughout all stages of evaporation, and substances which retary evaporation and (d) topnotes which are usually low-boiling, fresh-smelling materials. Such perfume compositions of our invention can be used in conjunction with carriers, vehicles, solvents, dispersants, emulsifiers, surface-active agents, aerosol propellants, and the like.

In perfume compositions the individual components contribute their particular olfactory characteristics, but the overall effect of the perfume composition will be the sum of the effect of each ingredient. Thus, one or more of α-oxy(oxo) sulfides of our invention can be used to alter, augment, modify or enhance the aroma characteristics of a perfume composition or a perfumed article, for example, by highlighting or moderating the olfactory reaction contributed by another ingredient of the composition.

The amount of one or more of the α-oxy(oxo) sulfides of our invention which will be effective in perfume compositions depends upon many factors, including the other ingredients, their amounts and the effects which are desired. It has been found that perfume compositions containing as much as 2% or as little as 0.005% by weight of the mixtures or compounds of this invention, or even less can be used to impart a buchu leaf oil-like aroma or a grapefruit oil-like aroma to soaps, cosmetics and other products. The amount employed will depend upon considerations of cost, nature of the end products, the effect desired in the finished product, and the particular fragrance sought.

One or more of the α-oxy(oxo) sulfides of our invention as disclosed herein can be used alone, in a fragrance modifying composition, or in a perfume composition as an olfactory component in detergents (anionic detergents, cationic detergents, and nonionic detergents) and soaps; space deodorants; perfumes; colognes; bath preparations such as bath oil, bath salts; hair preparations such as lacquers, brilliantines, pomades and shampoos; cosmetic preparations such as creams, deodorants, hand lotions, sun screens; powders such as talcs, dusting powders, face powders and the like. When one or more of the α-oxy(oxo) sulfides of our invention is used in perfumed articles such as the foregoing, it can be used in amounts of 0.01% or lower. Generally, it is preferred not to use more than about 2% in the finished perfumed article, since the use of too much will tend to unbalance the total aroma and will needlessly raise the cost of the article.

The following examples serve to illustrate embodiments of the invention as it is now preferred to practice it. It will be understood that these examples are illustrative and the invention is to be considered restricted thereto only as indicated in the appended claims.

EXAMPLE I

(A) PREPARATION OF 3-CHLORO-4-HEPTANONE

Reaction:

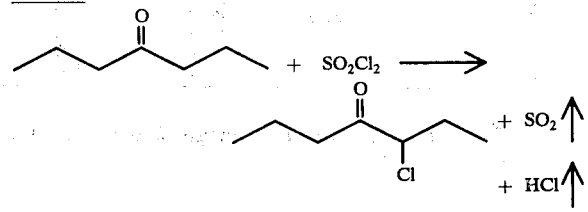

Into a 3000 ml, three-necked, round bottom flask, equipped with mechanical stirrer, 500 ml addition funnel, Y-tube, pot thermometer and gas outlet tube with rubber tubing leading over a stirring solution of 10% sodium hydroxide is added 1000g 4-heptanone. Addition of 434 g of $SO_2Cl_2$ drop-wise into the 4-heptanone is commenced while maintaining the pot temperature in the range of 22°–34° C and is continued over a period of two hours. A water aspirator vacuum is applied to the reaction mass in order to pull the acidic gases, sulfur dioxide and hydrogen chloride, over the sodium hydroxide solution.

The reaction mass is periodically sampled using GLC analysis until such time as about 25% chlorinated ketone product is found to be present.

While maintaining the reaction mass at 15° C, 1000 ml saturated sodium chloride is added to the mixture, and the mixture is then stirred for a period of 10 minutes. The reaction mass is then transferred to a 5-liter separatory funnel and shaken well, whereupon the organic and aqueous phases separate. The lower aqueous phase (approximately 1000 ml) has a pH of about 1. The upper organic phase is washed with 700 ml saturated sodium bicarbonate solution to a pH of 6–7. The organic phase is then dried over 50 grams anhydrous sodium sulfate and filtered yielding a yellow oil weighing 1063 grams. The organic layer is determined to contain 24.9% chlorinated ketone and 68.1% original ketone starting material. This material is then vacuum distilled by first adding it to a 2000 ml, three-necked, round-bottom flask equipped with a 2.5 × 60 cm vacuum jacketed column packed with 6 mm Raschig Rings, and equipped with an automatic reflux head, a pot thermometer, a heating mantle, a vacuum pump and a dry-ice trap. Fractionation data is as follows:

| Vacuum (mmHg) | Pot Temp. | Vapor Temp. | Weight of Fraction | Cut. No. | Reflux Ratio |
|---|---|---|---|---|---|
| 62 | 80 | 71 | 51.0 g | 1 | 60:40 |
| 62 | 81.5 | 71 | 149.0 g | 2 | 40:60 |
| 58 | 82.5 | 70 | 157.5 g | 3 | 30:70 |
| 59 | 89.5 | 70 | 175.0 g | 4 | 30:70 |
| 59 | 96 | 75 | 110 g | 5 | 30:70 |
| 59 | 100 | 80 | 24.5 g | 6 | 50:50 |
| 58 | 101 | 90 | 16.0 g | 7 | 50:50 |
| 58 | 102 | 94 | 37.5 g | 8 | 30:70 |
| 55 | 103 | 94 | 144.5 g | 9 | 30:70 |
| 54 | 110 | 95 | 85.0 g | 10 | 30:70 |
| 54 | 119 | 102 | 28.0 g | 11 | 30:70 |
| 15 | 140 | 80 | 45.0 g | 12 | 30:70 |

GLC analysis on each of cuts 5–12 (conditions 8 feet × ¼ inch SE-30 column) yields the following information:

| Cut No. | Percent low Boilers | Percent 4-Heptanone | Percent 3-Cl 4-Heptanone | Percent High Boiler (A) | Percent High Boiler (B) | Percent High Boiler (C) | Percent High Boiler (D) |
|---|---|---|---|---|---|---|---|
| 5 | 0.09 | 96.15 | 2.97 | — | — | — | — |
| 6 | | | | | | | |
| 7 | | 50% | 50% | | | | |
| 8 | — | 9.28 | 87.09 | 2.43 | 0.57 | — | — |
| 9 | — | trace | 95.78 | 3.22 | 1.00 | — | — |
| 10 | — | — | 91.38 | 4.89 | 3.34 | 0.21 | — |
| 11 | — | — | 69.14 | 7.27 | 19.88 | 3.71 | — |
| 12 | — | — | 8.32 | 2.07 | 49.28 | 39.69 | 0.47 |

Cuts 8, 9 and 10 are blended (weight 266.5 gms) and are analyzed as follows:

| | |
|---|---|
| 0.95% | 4-heptanone |
| 93.89% | 3-chloro-4-heptanone |
| 3.60% | high boiler A |
| 1.57% | high boiler B |

B. PREPARATION OF 3-THIOACETYL-4-HEPTANONE

Reaction:

$$CH_3-\overset{O}{\underset{\|}{C}}-SH + NaOCH_3 \xrightarrow{CH_3OH}$$

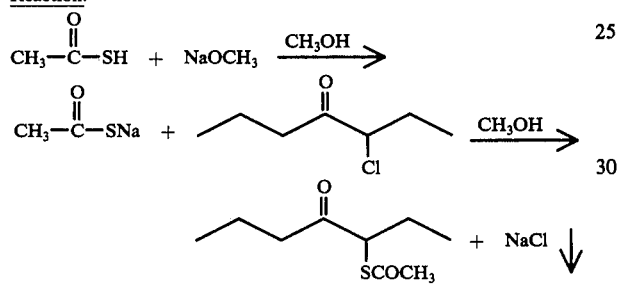

Into a 25 ml, three-necked, round-bottom flask equipped with magnetic stirrer, nitrogen inlet tube, 6 inch Vigreux column with cotton plug and pot thermometer is added a solution of 0.27 grams sodium methoxide in 3 ml anhydrous methanol (0.005 moles sodium methoxide). Under dry nitrogen, 0.38 grams of thioacetic acid dissolved in 3 ml anhydrous methanol (0.005 moles thioacetic acid) is then added to the sodium methoxide solution over a 2-minute period. A solution of 3-chloro-4-heptanone in methanol (0.75 grams 3-chloro-4-heptanone dissolved in one ml anhydrous methanol) prepared according to Part A, supra (cuts 8, 9 and 10 blended) is then added to the reaction mass which becomes turbid. Stirring is continued for a period of 1 hour, whereupon GLC analysis (conditions: 8 feet × ¼ inch SE-30 column) yields the following data:

| | |
|---|---|
| 15.6% | 3-chloro-4-heptanone |
| 3.0% | chloro heptanone high boiler |
| 77.67% | major peak |
| 2.37% | late peak |

With stirring, 15 ml water is added to the reaction mass which then splits up into two phases, an aqueous phase and an organic phase. The pH of the aqueous phase is 5–6. The organic phase is extracted with two 10 ml portions of methylene chloride. The methylene chloride extracts are combined and washed with 5 ml saturated sodium chloride solution. The organic phase is then dried over anhydrous sodium sulfate and concentrated in a rotary evaporator using water aspirator vacuum yielding 0.65 grams of a dark amber oil. GLC trapping of the major peak (Conditions: 8 feet × ¼ inch SE-30 column operated at 120° C, programmed at 5° C/minute) yields a compound having a molecular weight of 188 and having a mass spectral analysis, NMR analysis and IR analysis which causes confirmation of the structure:

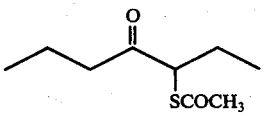

The NMR spectrum is set forth in FIG. 1.
The infrared spectrum is set forth in FIG. 2.
The NMR analysis is as follows:

3-thioacetyl-4-heptanone

| | | | |
|---|---|---|---|
| 0.92 ppm | (t) | $CH_3-CH_2$ | } 6H |
| 0.96 | (t) | $CH_3-C-C-S$ | |
| 2.01–1.44 | (m) | $-CH_2-$ | } 4H |
| 2.39 | (s) | $CH_3-\overset{O}{\underset{\|}{C}}-S$ | } 5H |
| 2.53 | (m) | $-CH_2-\overset{O}{\underset{\|}{C}}-$ | |
| 4.20 | (t) | $O=C-HC-S-C=O$ | 1H |

The IR analysis is as follows:
620 CM$^{-1}$, 950, 1125, 1350, 1450, 1690, 2320, 2870, 2930, 2960.

Material prepared similarly to above example was vacuum distilled yielding 99.3% pure product (boiling point 93.5°–94.5° C at 2.8 mm Hg). The thus-distilled material has the same physical properties as set forth above for 3-thioacetyl-4-heptanone.

(C) PREPARATION OF 3-THIOMETHYL-4-HEPTANONE

Reaction:

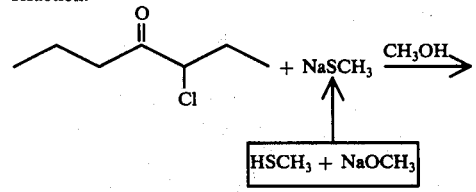

-continued

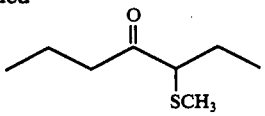

Into a 50-ml, three-necked, round-bottom flask equipped with magnetic stirrer, dry ice condenser, pot thermometer, cold water bath, reflux condenser with nitrogen inlet tube and nitrogen bubbler, is placed a solution of 0.54 grams of sodium methoxide in 6 ml anhydrous methanol (0.01 moles sodium methoxide). The sodium methoxide solution is then cooled using the cold-water bath to a temperature of 25° C. The nitrogen flow is ceased and methyl mercaptan in methanol (0.48 grams methyl mercaptan in 6 ml anhydrous methanol, 0.01 moles methyl mercaptan) is added to the reaction mass while maintaining same at 24° C. At 24° C, a solution of 1.49 grams of 3-chloro-4-heptanone in 2 ml anhydrous methanol (0.01 moles 3-chloro-4-heptanone) is added to the reaction mass. The 3-chloro-4-heptanone is produced according to the process set forth in part (A), supra. The reaction mass is maintained, with stirring, at 25° C for a period of 1 hour and 15 minutes. At the end of this period, the reaction mass is flushed with nitrogen. The reaction mass is then concentrated on a rotary evaporator using a water aspirator vacuum to approximately 5 ml.

Distilled water (15 ml) is then added to the concentrated reaction mixture whereupon the reaction mixture forms into two phases; an oil phase and an aqueous phase. The pH of the aqueous phase is in the range of 5–6. The oil phase is then extracted with two 12 ml portions of n-hexane and the phases are separated. The hexane extracts are combined, washed with water (5 ml), dried over anhydrous sodium sulfate, gravity filtered and concentrated on a rotary evaporator to a weight of 1.29 grams. The resulting product contains a 90.1% 3-thiomethyl-4-heptanone by GLC having the structure:

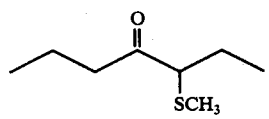

as confirmed by NMR, IR and mass spectral analyses of trapped compound.

The NMR spectrum is set forth in FIG. 3. The IR spectrum is set forth in FIG. 4.

The NMR analysis is as follows:

| 3-thiomethyl-4-heptanone | | | 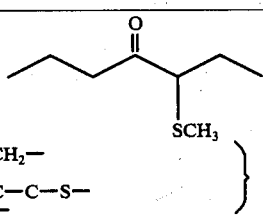 | |
|---|---|---|---|---|
| 0.94 ppm | (t) | CH$_3$—CH$_2$— | | 6H |
| 0.97 | (t) | CH$_3$—C—C—S— | | 4H |
| 1.68 | (m) | —CH$_2$— | | 4H |
| 1.92 | (s) | CH$_3$—S— | | 3H |
| 2.60 | (m) | —CH$_2$—C(=O)— | | 2H |
| 3.08 | (t) | C—HC—S—, ||O | | 1H |

The IR analysis is as follows:
1360 cm$^{-1}$, 1375, 1455, 1690, 2330, 2880, 2930, 2960.

Material prepared similarly to above example was vacuum distilled yielding 99.2% pure product (boiling point 78°–78.5° C at 8.5 mm Hg). The thus-distilled material has the same physical properties as set forth above for 3-thiomethyl-4-heptanone.

(D) PREPARATION OF 3-THIOMETHYL-4-HEPTANOL

Reaction:

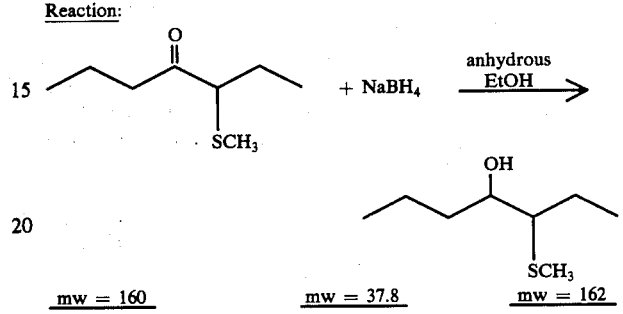

mw = 160    mw = 37.8    mw = 162

Into a 25 ml, three-necked, round-bottom flask equipped with magnetic stirrer, nitrogen inlet tube, reflux condenser, pot thermometer and cold water bath, is added a solution of 0.10 grams sodium borohydride (NaBH$_4$) dissolved in 4 ml anhydrous ethyl alcohol (0.00265 moles sodium borohydride). While maintaining the pot temperature at 25° C, a solution of 0.8 grams of 3-thiomethyl-4-heptanone in 3.5 ml anhydrous ethyl alcohol is added to the sodium borohydride-ethanol solution over a one-minute period. The reaction mass then warms up to about 30° C and is maintained at a temperature of between 25° and 30° C for a period of about 1.5 hours. At the end of this period another 0.05 grams (0.00133 moles) of sodium borohydride and 2 ml ethanol is added.

After 10 minutes of stirring while maintaining the reaction mass at 25° C, the reaction mass is then worked up as follows: The reaction mixture is concentrated to about 4 ml of a thick slurry using water aspirator vacuum. The resulting thick slurry is then combined with 12 ml water thereby causing the solid to dissolve, and the reaction mass to exist in two phases; an aqueous phase and an organic phase. The aqueous phase is acidified to a pH of 2–3 using 10% HCl solution. The organic phase is extracted with two 12 ml portions of methylene chloride. The extracts are then combined, washed with 8 ml water, dried over anhydrous sodium sulfate, gravity filtered, and then concentrated on a rotary evaporator (using water aspirator vacuum) to a weight of 0.58 grams. The desired product is trapped out on an 8 feet × ¼ inch SE-30 GLC column; and MS, NMR and IR analyses confirm that the resulting compound has the structure:

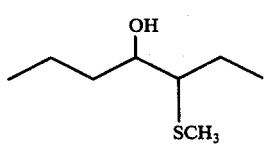

The NMR spectrum is set forth in FIG. 5. The infrared spectrum is set forth in FIG. 6.

The NMR analysis is as follows:

| | | | |
|---|---|---|---|
| 0.94 ppm | (t) | CH₃—CH₂— | |
| | | | 6H |
| 1.06 | (t) | CH₃—C—C—S— | |
| 1.51 | (m) | —CH₂— | 6H |
| 2.06 | (s) | CH₃—S— | 3H |
| 2.36 | (m) | HC—S— | |
| | | | 2H |
| 2.62 | (broad) | —OH | |
| 3.52 | (m) | HC—O— | 1H |

The IR analysis is as follows:
980 cm⁻¹, 1010, 1065, 1370, 1430, 1450, 2320, 2860, 2920, 2960, 3440.

Material prepared similarly to above example was vacuum distilled yielding 99.5% pure product (boiling point 64°-64.5° C at 1.5 mm Hg). The thus-distilled material has the physical properties as set forth above for 3-thiomethyl-4-heptanol. cl EXAMPLE II

PREPARATION OF
3-METHALLYLTHIO-2,6-DIMETHYL-4-HEPTANONE (A) Preparation of 3-chloro-2,6-dimethyl-4-heptanone

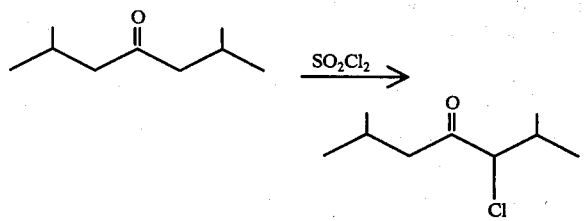

Into a one-liter, three-necked, round-bottom flask equipped with "Y" tube, pot thermometer, mechanical stirrer, 125 ml addition funnel, gas outlet tube, cold water bath and water aspirator vacuum is added 356 grams of 2,6-dimethyl-4-heptanone (2.4 moles). Over a period of one hour, 67.5 grams (40 ml; 0.5 moles) of SO₂Cl₂ is slowly added to the ketone with stirring while maintaining the reaction mass temperature in the range of 23°-35° C.

The reaction mass is then evacuated slowly using water aspirator vacuum thereby removing most of the acidic gases resulting from the foregoing reaction.

The reaction mass is then transferred to a one-necked, one-liter, round-bottom flask and the last traces of acidic gases are removed thus yielding 371 grams of product. The reaction mass is then transferred to a 500 ml, three-necked, round-bottom flask equipped with a 2.0 × 30 cm column packed with ⅛ inch helioes, reflux head, magnetic stirrer, heating mantle and vacuum pump and the resulting 3-chloro-2,6-dimethyl-4-heptanone is fractionally distilled at a vapor temperature of 106°-107° C and a pressure of 45-46 mm Hg yielding a product of 97% purity as confirmed by GLC, mass spectral, NMR and IR analyses.

B. PREPARATION OF
3-MERCAPTO-2,6-DIMETHYL-4-HEPTANONE

Reaction:

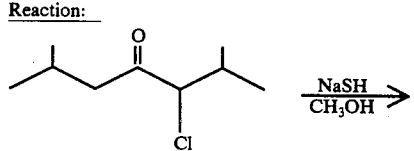

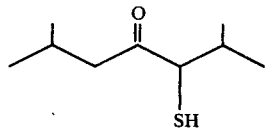

Into a 250 ml, round-bottom, three-necked flask equipped with magnetic stirrer, pot thermometer, 6 inch Vigreux distillation column with gas outlet at top leading over 200 ml 10% sodium hydroxide solution, H₂S gas inlet tube (sub-surface), "Y" tube, 50 ml addition funnel, gas bubbler, and dry ice-isopropyl alcohol bath, and cold water bath is added a solution of 11.6 grams of sodium methoxide dissolved in 90 ml anhydrous methanol. The sodium methoxide solution is cooled to a temperature of −15° C using the dry ice-isopropanol bath. While maintaining the temperature of the sodium methoxide solution at −10° to −5° C, hydrogen sulfide is bubbled into the reaction mass over a period of 2 hours. While continuing to bubble in hydrogen sulfide and maintaining the reaction mass at a temperature in the range of −5° to −9° C, the 3-chloro-2,6-dimethyl-4-heptanone prepared in Part A of this example (18.2 grams; 0.100 moles) is added slowly to the reaction mass from the addition funnel over a period of 13 minutes. The reaction mass is then maintained at a temperature of 0°-26° C for a period of 4 hours (25°-26° C for the last 1.5 hours).

The reaction mass is then concentrated to approximately 25 ml (thick slurry) using a rotary evaporator and water aspirator vacuum. 85 ml distilled water is then added to the reaction mass, with stirring, while maintaining the temperature at 25° C, thereby yielding a turbid yellow solution. 85 grams of 10% aqueous sodium hydroxide is then added to the resulting mixture whereupon the temperature rises from 25° to 28° C (pH = 10-11). The basic aqueous solution is then extracted with two 70 ml portions of methylene chloride and the extracts are combined, dried and concentrated yielding 1.7 grams of an oil. The basic aqueous solution is then acidified with 115 ml 10% hydrochloric acid to a pH of 1-2. This is then extracted with four 50 ml portions of methylene chloride. The methylene chloride extracts are combined and washed with two 35 ml portions of saturated sodium chloride (to a pH of 5) and dried over anhydrous sodium sulfate. The resulting mixture is gravity filtered and concentrated on a rotary evaporator to yield 15.5 grams of product containing 96.1% 3-mercapto-2,6-dimethyl-4-heptanone as confirmed by mass spectral, NMR and IR analyses. This material is vacuum distilled at a vapor temperature of 77.5°-78° C and a pressure of 6 mm Hg.

C. Preparation of
3-methallylthio-2,6-dimethyl-4-heptanone

Reaction:

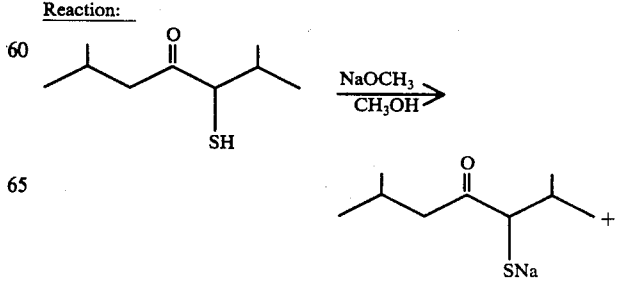

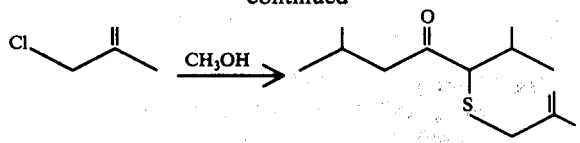

Into a 25 ml, three-necked, round-bottom flask equipped with magnetic stirrer, "Y" tube, nitrogen inlet, reflux condenser with cotton plug, cold water bath and warm water bath is added a solution of 0.162 grams of sodium methoxide dissolved in 2 ml anhydrous methanol. Over a period of 1 minute is added a solution of 0.522 grams of 3-mercapto-2,6-dimethyl-4-heptanone dissolved in 3 ml anhydrous methanol, with stirring. After stirring 12 minutes at 24°-25° C, a solution of 0.3 grams of 3-chloro-2-methyl propene in 1 ml anhydrous methanol is added. With a water bath, the resulting reaction mass is warmed to 31° C and the reaction mass is then stirred while maintaining the temperature in the range of 23°-30° C for a period of 2 hours.

The reaction mass is then concentrated on a rotary evaporator using water aspirator vacuum to approximately 4 ml yielding a slurry. To the slurry is added 8 ml water and the solid dissolves. The reaction mass is then acidified to a pH of 1-2 with 3 drops of 10% hydrochloric acid. The reaction mass is then extracted with three 8 ml portions of methylene chloride and the extracts are combined, washed with 10 ml water, dried over anhydrous sodium sulfate and gravity filtered. The extracts are concentrated on a rotary evaporator to yield 0.54 grams of a white oil containing 93.6% by GLC of 3-methallylthio-2,6-dimethyl-4-heptanone as confirmed by MS, IR and NMR analyses of trapped product.

The NMR is set forth in FIG. 7. The infrared spectrum is set forth in FIG. 8.

The mass spectrum analysis is as follows:

| M/E | Relative Intensity |
| --- | --- |
| 41 | 29 |
| 55 | 44[3] |
| 57 | 37[6] |
| 69 | 10 |
| 85 | 43[5] |
| 87 | 93[2] |
| 109 | 33 |
| 142 | 44[4] |
| 143 | 100[1] |
| M 228 | 28 |

The NMR analysis is as follows:

| | | | | |
| --- | --- | --- | --- | --- |
| 1.92 ppm, 2.06 | (2 doublets) | H<br>CH$_3$—C— | | 12H |
| 1.78 | (s) | =C—CH$_3$ | | 3H |
| 2.12 | (m) | methine protons | | 2H |
| 2.47 | (t) | —CH$_2$— | | 2H |
| 2.82 | (d) | O=C—C—S—<br>  H | | 1H |
| 3.01 | (s) | =C—CH$_2$—S— | | 2H |
| 4.86 | (s) | C=C$\genfrac{}{}{0pt}{}{H}{H}$ | | |

The IR analysis is as follows:
890 cm$^{-1}$, 1035, 1160, 1200, 1225, 1285, 1360, 1380, 1400, 1460, 1640, 1695, 2870, 2960, 3080.

Material prepared similarly to above example was vacuum distilled yielding 99.8% pure product (boiling point 100°-105° C at 1.3 mm Hg). The thus-distilled material has the same physical properties as set forth above for 3-methallylthio-2,6-dimethyl-4-heptanone.

EXAMPLE II

D. PREPARATION OF 3-THIOACETYL-2,6-DIMETHYL-4-HEPTANONE

Reaction:

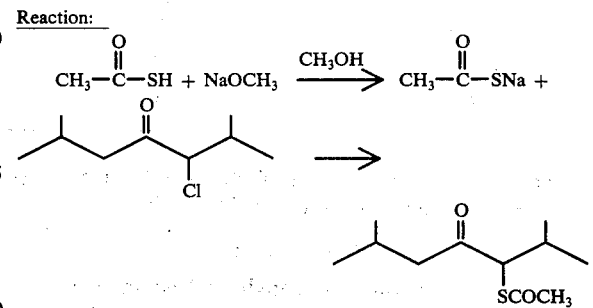

Into a 25 ml, three-necked, round-bottom flask equipped with magnetic stirrer, nitrogen inlet tube at top of 6 inch Vigreux column, reflux condenser with cotton plug, pot thermometer, water bath and heating mantle is placed a solution containing 0.27 grams of sodium methoxide (0.005 moles) in 3 ml anhydrous methanol. To the sodium methoxide solution is added a solution of 0.38 grams (0.005 moles) of thioacetic acid in 3 ml anhydrous methanol, with stirring, while maintaining the reaction mass temperature in the range of 23°-25° C. The addition takes place over a period of 10 minutes. While maintaining the reaction mass temperature at 23° C, a solution of 0.883 grams (0.005 moles) of 3-chloro-2,6-dimethyl-4-heptanone (prepared according to Part A) in 2 ml anhydrous methanol is added to the reaction mass. While maintaining the reaction mass temperature between 35° and 45° C and over a period of 3 hours, the reaction mass is stirred. At the end of the 3-hour period only 6% of product is formed. The reaction mass is then refluxed at 66°-76° C for a period of 12 hours, at which point it is indicated by GLC, NMR, IR and mass spectral analyses that 3-thioacetyl-2,6-dimethyl-4-heptanone is formed in an amount of 65%.

The reaction mass is then concentrated on a rotary evaporator using water aspirator vacuum to 4 ml of an oily product. Ten ml water is then added, and the solid dissolves. The oil layer is extracted with three 8 ml portions of methylene dichloride, and the extracts are combined and washed with one 8 ml water portion. The extracts are then dried over anhydrous sodium sulfate, gravity filtered and concentrated yielding 0.54 grams of a yellow oil. The desired product is trapped on a GLC SE-30 column (Conditions: 8 feet × ¼ inch).

The NMR analysis is as follows:

| | | |
| --- | --- | --- |
| 1.01–0.88 ppm | Methyl protons | 12H |
| 2.42–2.03 | Methine protons | |
| 2.44 | CH$_2$—C—<br>  ‖<br>  O | 7H |
| 2.40 | O<br>‖<br>CH$_3$—C—S— | |
| 4.14 | 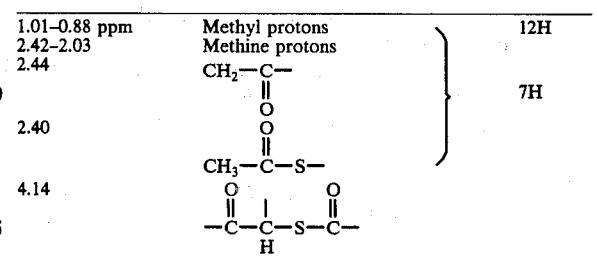 | |

The infrared analysis is as follows:

6.20 cm⁻¹, 950, 1100, 1130, 1360, 1380, 1465, 1695, 2870, 2930, 2960.

The mass spectral analysis is as follows:

| M/E | Relative Intensity |
|---|---|
| 41 | 14[5] |
| 43 | 40[3] |
| 55 | 12 |
| 57 | 60[2] |
| 85 | 100[1] |
| 89 | 27[4] |
| 131 | 12[6] |
| 141 | 9 |
| 173 | 11 |
| M 216 | 7 |

The NMR spectrum is set forth in FIG. 8(A). The infrared spectrum is set forth in FIG. 8(B).

EXAMPLE III

A. Preparation of 3-propylthio-4-heptanone

Reaction:

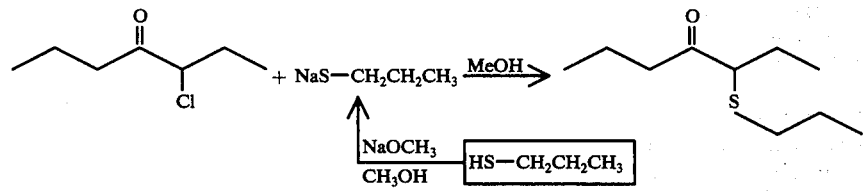

Into a 50 ml, three-necked, round bottom flask equipped with magnetic stirrer, reflux condenser, nitrogen inlet tube, pot thermometer and cold water bath, is placed a solution of 0.54 grams of sodium methoxide dissolved in 6 ml anhydrous methanol (0.01 moles of sodium methoxide). The sodium methoxide solution is cooled using the water bath to 25° C. A solution of 0.76 grams of n-propyl mercaptan dissolved in 6 ml anhydrous methanol (0.01 moles n-propyl mercaptan) is then added to the sodium methoxide/methanol solution, and the temperature rises to 28° C. 1.5 g (0.01 moles) 3-chloro-4-heptanone dissolved in 2 ml anhydrous methanol is then added, and the temperature of the reaction mass rises to 38° C, whereupon it is cooled using the water bath to a temperature in the range of 25°–30° C. The reaction mass is then stirred under nitrogen for a period of 6 hours.

The reaction mass is then concentrated to a volume of 4 ml using a rotary evaporator to which water aspirator vacuum is applied. 9 ml distilled water is then added to the reaction mass concentrate whereupon the solid dissolves. The oil phase is extracted with three 8 ml portions of methylene chloride, and the extracts are combined and washed with 8 ml of water and dried over anhydrous sodium sulfate and filtered and then concentrated. GLC, MS, NMR and IR analyses of trapped product yield the information that the subject material is 3-propylthio-4-heptanone The NMR spectrum is set forth in FIG. 9. The IR spectrum is set forth in FIG. 10.

The NMR analysis is as follows:

| | | | |
|---|---|---|---|
| 0.87–1.04 ppm | superimposed signals | CH₃— | 9H |
| 1.63 | (m) | —CH₂— | 6H |
| 2.38 | (t) | —CH₂—S— | 2H |
| 2.60 | (t) | $\underset{\text{O}}{\overset{\text{O}}{\underset{\|}{\text{CH}_2-\overset{\|}{\text{C}}-}}}$ | 2H |
| 3.11 | (t) | O=C—HC—S— | 1H |

The IR analysis is as follows:
1130 cm⁻¹, 1165, 1290, 1360, 1380, 1405, 1460, 1700, 2880, 2940, 2960.

The mass spectral analyses is as follows:

| M/E | Relative Intensity |
|---|---|
| 41 | 20[4] |
| 43 | 26[3] |
| 55 | 5 |
| 71 | 10 |
| 75 | 35[2] |
| 114 | 10 |
| 117 | 100[1] |
| 118 | 10[6] |
| 119 | 9 |
| M 188 | 16[5] |

Material prepared similarly to above example was vacuum distilled yielding 98.4% pure product (boiling point 72°–73° C at 1.5 mm Hg). The thus-distilled material has the same physical properties as set forth above for 3-propylthio-4-heptanone.

B. Preparation of 3-propylthio-4-heptanol

Reaction:

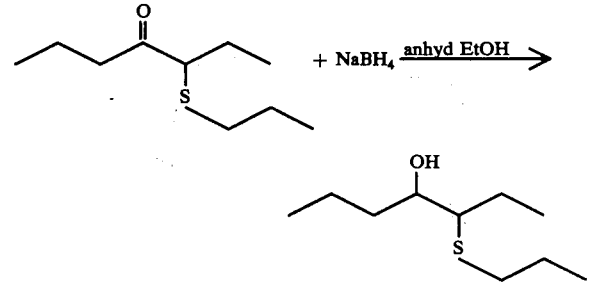

Into a 25 ml, three-necked, round bottom flask equipped with magnetic stirrer, reflux condenser, pot thermometer, and nitrogen inlet (for flushing with dry nitrogen) is added a solution of 0.15 grams of sodium borohydride dissolved in 6 ml anhydrous methanol (0.004 moles sodium borohydride). With stirring, a solution of 1.0 grams of 3-propylthio-4-heptanone dissolved in 4 ml anhydrous ethyl alcohol is added to the sodium borohydride solution which then warms to 28° C. The reaction mass is stirred for a period of 2 hours at 25° C and then concentrated on a rotary evaporator (using water aspirator vacuum) to a volume of 4 ml yielding an oily solid. 8 ml water is then added to the solid, with stirring, and the solid dissolves yielding two phases: an oil phase and a water phase. The resulting reaction mass is acidified with 10% hydrochloric acid to a pH of between 2 and 3. The oil phase is extracted with three 8 ml volumes of methylene chloride, and the extracts are combined and washed with 8 ml water. The extracts are then dried over anhydrous sodium sulfate, filtered and concentrated to a weight of 0.79 grams (water-white oil). GLC, IR, mass spectral and NMR analyses after GLC trapping (conditions: 8 feet × ¼ inch SE-30 column) yield the information that the crude material is 96% product having the structure of 3-propylthio-4-heptanol.

The NMR spectrum is set forth in FIG. 11. The IR spectrum is set forth in FIG. 12.

The NMR analysis is as follows:

| 1.13–0.96 ppm | superimposed signals | methyl protons | 9H |
|---|---|---|---|
| 1.44 | (m) | —CH₂— | 8H |
| 2.47 | (s) | —OH | |
| | | | 4H |
| 2.49 | (m) | HC—S—CH₂— | |
| 3.50 | (m) | HC—O— | 1H |

The IR analysis is as follows:
1290 cm⁻¹, 1380, 1460, 2880, 2940, 2970, 3460.

Material prepared similarly to above example was vacuum distilled yielding 99.8% pure product (boiling point 65° C at 0.4 mm Hg). The thus-distilled material has the same physical properties as set forth above for 3-propylthio-4-heptanol.

EXAMPLE IV

PREPARATION OF 3-ISOBUTYLTHIO-4-HEPTANONE lowed to cool to a temperature of 24° C and stirred at that temperature for a period of 6 hours.

The reaction mass is then concentrated on a rotary evaporator using water aspirator vacuum to a volume of 4 ml yielding an oily solid. Ten ml water is then added, and the solid dissolves yielding two phases: an oil phase and an aqueous phase. The oil phase is extracted with three 9 ml portions of methylene chloride, and the extracts are combined and washed with 9 ml water. The extracts are then dried over anhydrous sodium sulfate, filtered and concentrated to a weight of 1.78 grams.

Mass spectral, infrared, NMR and IR analyses yield the information that the reaction mass contains 90.9% product which is 3-isobutylthio-4-heptanone.

The NMR spectrum is set forth in FIG. 13. The IR spectrum is set forth in FIG. 14.

The NMR analysis is as follows:

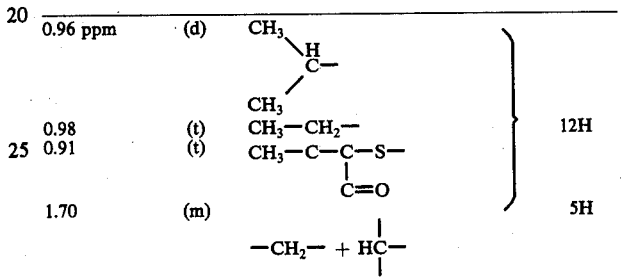

| 0.96 ppm | (d) | CH₃\ H /C— CH₃ | |
|---|---|---|---|
| 0.98 | (t) | CH₃—CH₂— | 12H |
| 0.91 | (t) | CH₃—C—C—S— \| C=O | |
| 1.70 | (m) | —CH₂— + HC— | 5H |

Reaction:

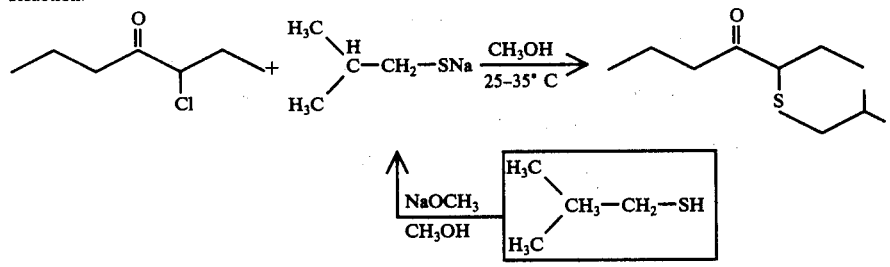

Into a 50 ml, three-necked, round bottom flask equipped with magnetic stirrer, reflux condenser, pot thermometer, water bath, 15 cm Vigreux column with nitrogen inlet at top is added a solution of 0.54 grams of sodium methoxide (0.01 moles) in 6 ml anhydrous methanol. The reaction mass is cooled to 25° C and a solution of 0.90 grams of isobutyl mercaptan (2-methyl-1-propanethiol) dissolved in 6 ml anhydrous methanol is added over a period of 1 minute. After keeping the reaction mass at 24° C with stirring for a period of 10 minutes, 1.50 grams of 3-chloro-4-heptanone dissolved in 2 ml anhydrous methyl alcohol (0.01 moles of 3-chloro-4-heptanone) is added to the reaction mass which then warms to 37° C. The reaction mass is al-

| 2.26 | (d) | S—CH₂— | 2H |
|---|---|---|---|
| 2.60 | (t) | —CH₂—C— ‖ O | 2H |
| 3.10 | (t) | O=C—HC—S— | 1H |

The IR analysis is as follows:
1365 cm⁻¹, 1380, 1460, 1700, 2880, 2940, 2960.

EXAMPLE V

A. PREPARATION OF 3-ISOBUTYLTHIO-2,6-DIMETHYL-4-HEPTANONE

Reaction:

-continued

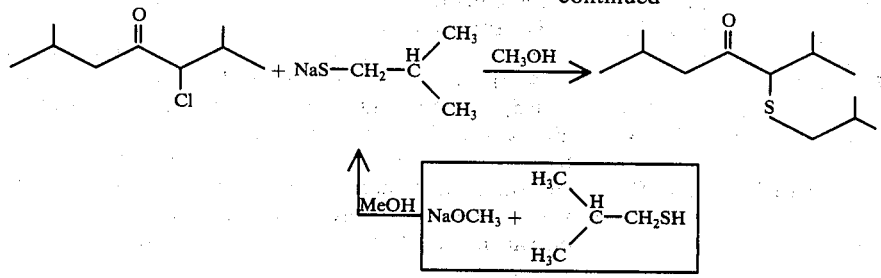

Into a 50 ml, three-necked, round bottom flask equipped with pot thermometer, magnetic stirrer, gas inlet tube (for nitrogen) at top of 15 cm Vigreux column, nitrogen bubbler and cold water bath is added a solution of 0.54 grams (0.01 moles) of sodium methoxide dissolved in 6 ml anhydrous methanol. The solution is cooled to 24° C and a solution of 0.90 grams (0.01 moles) of isobutyl mercaptan dissolved in 6 ml anhydrous methanol is then added to the reaction mass. After stirring at 24° C for a period of 10 minutes, a solution of 1.77 grams of 3-chloro-2,6-dimethyl-4-heptanone dissolved in 2 ml anhydrous methanol is added to the reaction mass with stirring at 24°–25° C. The reaction mass is then stirred for a period of 8 hours.

The reaction mass is then concentrated on a rotary evaporator using water aspirator vacuum to 5 ml of a thick oil/solid slurry. 15 ml water is added and the solid dissolves. The resulting liquid mixture being in 2 phases; an aqueous phase and an organic phase. The reaction mass is then extracted with three 10 ml portions of methylene dichloride and the extracts are combined and washed with 8 ml water. The extracts are then dried over anhydrous sodium sulfate, gravity filtered and concentrated on a rotary evaporator to a weight of 1.89 grams (pale yellow oil). GLC, NMR, IR and mass spectral analyses yield the information that the resulting product is 79.2% 3-isobutylthio-2,6-dimethyl-4-heptanone.

The NMR analysis is as follows:

| | | |
|---|---|---|
| 0.94 ppm, 1.10 | methyl protons | 18 H |
| 2.26 – 1.60 | methine protons | 3 H |
| 2.26 | —CH$_2$—S— | 2 H |
| 2.50 | —CH$_2$—C(=O)— | 2 H |
| 2.80 | HC—S, —C=O | 1 H |

The IR analysis is as follows:
1035 cm$^{-1}$, 1160, 1285, 1360, 1380, 1460, 1700, 2870, 2930, 2960.

The mass spectral analysis is as follows:

| M/E | Relative Intensity |
|---|---|
| 29 | 7 |
| 41 | 11[5] |
| 55 | 17[4] |
| 57 | 42[2] |
| 69 | 6 |
| 85 | 8 |
| 89 | 33[3] |
| 145 | 100[1] |
| 146 | 9[6] |
| M 230 | 8 |

The NMR spectrum is set forth in FIG. 14(A). The IR spectrum is set forth in FIG. 14(B).

B. PREPARATION OF 3-ISOBUTYLTHIO-2,6-DIMETHYL-4-HEPTANOL

Reaction:

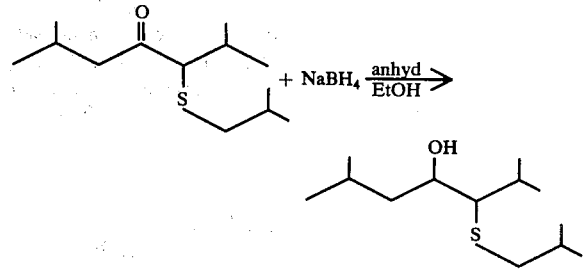

Into a 25 ml, three-necked, round-bottom flask equipped with magnetic stirrer, reflux condenser, pot thermometer and nitrogen inlet tube to flush with dry nitrogen, is added a solution of 0.1 grams (0.00265 moles) of sodium borohydride dissolved in 4 ml anhydrous ethanol. While the temperature of the sodium borohydride solution is at 24° C, a solution of 1.1 grams of 3-isobutylthio-2,6-dimethyl-4-heptanone (prepared according to Part A) dissolved in 4 ml anhydrous ethanol is added to the reaction mass slowly. The reaction mass is then stirred for a period of 6.5 hours.

The reaction then shows 30% product (3-isobutylthio-2,6-dimethyl-4-heptanol) by GLC analysis. An additional 0.2 grams of sodium borohydride dissolved in 6 ml anhydrous ethanol is added, and the reaction mass is continued to be stirred for a period of 4 hours. GLC analysis shows 59% product. Another 0.15 grams of sodium borohydride in 5 ml anhydrous ethanol is added and stirred for an additional 4 hours.

GLC analysis then shows 78% product.

The reaction mixture is then concentrated on a rotary evaporator using water aspirator vacuum to 5 ml of an oily solid. 6 ml water is then added and the solid dissolves yielding two liquid phases; an organic phase and an aqueous phase. The reaction mass is neutralized with 10% HCl to a pH of 5. The oil is then extracted with 20 ml methylene dichloride, and the extracts are washed with water. The extracts are then dried over anhydrous sodium sulfate, filtered and concentrated on a rotary evaporator to a weight of 0.82 grams (pale yellow oil). GLC analysis indicates that the material is 86.4% product. NMR and IR analyses of GLC trapped compound yield the information that the product is 3-isobutylthio-2,6-dimethyl-4-heptanol.

The NMR spectrum is set forth in FIG. 15. The IR spectrum is set forth in FIG. 16.

The NMR analysis is as follows:

| | | | |
|---|---|---|---|
| 1.10–0.89 ppm | super-imposed signals | CH$_3$— | 18H |
| 1.34 | (m) | methine protons | 3H |
| 1.84 | (m) | —CH$_2$—C—O— | 2H |
| 2.44 | (m) | —CH$_2$—S—, HC—S— | 3H |
| 2.79 | (broad) | —OH | 1H |
| 3.72 | (m) | HC—OH | 1H |

The IR analysis is as follows:
1055 cm$^{-1}$, 1365, 1385, 1465, 2880, 2930, 2960, 3460.

EXAMPLE VI

PREPARATION OF 3-METHYLTHIO-2,6-DIMETHYL-4-HEPTA-NONE

Reaction:

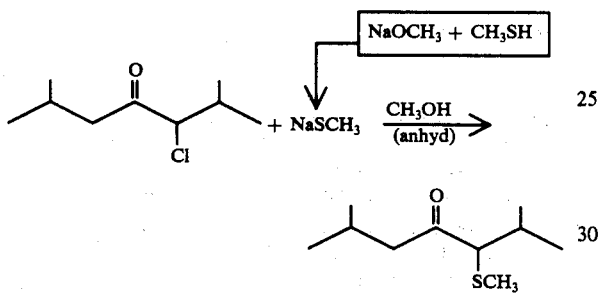

Into a 50 ml, three-necked, round-bottom flask equipped with pot thermometer, magnetic stirrer, gas inlet tube (sub-surface), gas bubbler, methyl mercaptan gas cylinder, 15 cm Vigreux column, gas outlet tube leading to stirred 10% sodium hydroxide solution, and cold water bath is added a solution of 0.54 grams of sodium methoxide in 12 ml anhydrous methanol (0.01 moles sodium methoxide). The reaction mass warms to 30° C, and it is cooled to 23° C using the cold water bath. Over a period of 20 minutes the methyl mercaptan is bubbled in below the surface of the liquid while maintaining the temperature of the reaction mass at 22°–23° C. The reaction flask is then flushed with dry nitrogen, and a solution of 1.77 grams of 3-chloro-2,6-dimethyl-4-heptanone dissolved in 2 ml anhydrous methanol is then added to the reaction mass. The reaction mass remains at 23°–25° C and is stirred at that temperature for a period of 2.5 hours. GLC analysis indicates 79% product. The reaction mass is then warmed to 35° C and maintained at 28°–35° C for another 1.5 hours.

The reaction mass is then concentrated to a volume of 5 ml using a rotary evaporator to which water aspirator vacuum is applied. 15 ml distilled water is then added to dissolve the solid yielding a two phase mixture (an aqueous phase and an organic phase). The reaction mass is then extracted with three 10 ml portions of methylene chloride, and the extracts are combined and washed with 10 ml of water. The combined extracts are then dried over anhydrous sodium sulfate, gravity filtered and concentrated on a rotary evaporator to a weight of 1.56 grams. GLC, MS, NMR and IR analyses yield the information that the resulting material is 89.6% product, 3-methylthio-2,6-dimethyl-4-heptanone. The pure material is trapped out using preparative GLC (conditions: 8 feet × ¼ inch SE-30 column).

The NMR spectrum is set forth in FIG. 17. The IR spectrum is set forth in FIG. 18.

The Mass Spectral analysis is as follows:

| M/E | Relative Intensity |
|---|---|
| 41 | 8[5] |
| 55 | 32[2] |
| 57 | 12[3] |
| 61 | 5 |
| 69 | 5 |
| 85 | 7[6] |
| 102 | 6 |
| 103 | 100[1] |
| 104 | 6 |
| M 188 | 10[4] |

The NMR analysis is as follows:

| | | |
|---|---|---|
| 0.94, 1.08 ppm | Methyl protons | 12 H |
| 1.90 | CH$_3$—S— | 3 H |
| 2.37 – 1.96 2.49 | Methine protons | 2 H |
| 2.78 | CH$_2$—C(=O)— HC—S— —C=O | |

The IR analysis is as follows:
1035 cm$^{-1}$, 1160, 1360, 1380, 1400, 1465, 1695, 2870, 2920, 2960.

EXAMPLE VII

OTTO OF ROSE PERFUME FORMULATION

The following mixture is prepared:

| Ingredients | Parts by Weight |
|---|---|
| Phenyl acetic acid | 5 |
| Hydroxycitronellal | 10 |
| Geraniol | 125 |
| Citronellol | 150 |
| Phenyl ethyl alcohol | 50 |
| Phenyl ethyl acetate | 4 |
| Ethyl phenyl acetate | 5 |
| Citronellyl formate | 20 |
| Geranyl acetate | 25 |
| Linalool | 15 |
| Terpineol | 10 |
| Eugenol | 3 |
| Phenyl acetaldehyde dimethyl acetal | 5 |
| Benzyl acetate | 3 |
| Guaiacwood Oil | 5 |
| 3-methylthio-4-heptanone produced according to the process of Part "C" of Example I | 10 |

The 3-methylthio-4-heptanone, produced according to the process of Part "C" of Example I imparts a green, fruity, spicy topnote so characteristic or rose otto to this formulation.

EXAMPLE VIII

ORIENTAL VETIVERT

The following mixture is prepared:

| Ingredients | Parts by Weight |
|---|---|
| Orange oil Florida | 150 |
| Lemon Oil | 75 |
| Oil of bitter orange | 100 |
| Grapefruit oil | 200 |
| Neroli oil | 20 |
| Isocyclemone E (a product produced according to the process of Example VI of U.S. Pat. 3,907,321, issued on Sept. 23, 1975, which comprises reacting myrcene with 3-methyl-3-pentene-2-one in | |

-continued

| Ingredients | Parts by Weight |
|---|---|
| the presence of aluminum chloride and then cyclizing the resulting Diels-Alder adduct.) | 40 |
| Gamma methyl ionone | 15 |
| Ylang extra | 5 |
| Auralva (The Shiff base of methyl anthranilate and hydroxy citronellal, specifically described in Section 1735 of Arctancer, "Perfume and Flavor Chemicals (Aroma Chemicals)" 1969) | 15 |
| Lyral 4-(4-methyl,4-hydroxyamyl) Δ³-cyclohexene carboxaldehyde | 30 |
| Grisalva (produced by the 50% sulfuric acid treatment of 3-ethyl-1[2,2,6-trimethyl-cyclohexene-5-yl-1]hexen-3-ol-6) | 10 |
| 3-(methallylthio)-2,6-dimethyl-4-heptanone, produced according to the process of Example II(C). | 50 |

The 3-(methallylthio)-2,6-dimethyl-4-heptanone, produced according to the process of Example II(C) imparts a sweet, orange-flower, green beta vetivone woody character to this composition.

EXAMPLE IX

NARCISSE FORMULATION

The following mixture is prepared:

| Ingredient | Parts by Weight |
|---|---|
| Benzyl alcohol | 50 |
| Benzyl benzoate | 25 |
| Terpineol | 30 |
| Nerol | 15 |
| Phenyl ethyl alcohol | 50 |
| Geraniol | 40 |
| Linalool | 50 |
| Para cresyl phenyl acetate | 10 |
| Benzyl acetate | 6 |
| Acetyl isoeugenol | 20 |
| Heliotropin | 30 |
| Ylang extra | 5 |
| Para cresol | 1 |
| 3-methylthio-4-heptanol, produced according to the process of Example I, Part "D" | 20 |

The 3-methylthio-4-heptanol, produced according to the process of Example I, Part "D" imparts a green, floral, heady tobacco-like oriental middle and undertone necessary for narcisse.

EXAMPLE X

COMPARISON OF SUBSTITUTED THIOHEPTANONES AND THEIR CORRESPONDING ALCOHOLS 3-methylthio-4-heptanone (hereinafter referred to as "chemical I") has a powerful green, minty, herbaceous odor. 3-methylthio-4-heptanol (hereinafter referred to as "chemical II") has a green, floral, herbal odor, about one-fifth the strength of chemical I. 3-(methallythio)2,6-dimethyl-4-heptanone (hereinafter referred to as "chemical III") has a floral, herbaceous aroma with a fruity, grapefruit (nootkatone) character.

The foregoing materials, chemicals I, II and III may be used in perfumery to give unusual and novel effects to various fragrance types. They are useful in creating modern blends which are in some cases far removed from the classical concepts of perfumery. The use of chemicals I, II and III may be demonstrated in the following modern herbal formulation:

| Ingredients | A | B | C |
|---|---|---|---|
| Oakmoss Absolute 50% in diethylphthalate | 20 | 20 | 20 |
| α-methyl-3,4-methylene-dioxy-hydrocinnamic aldehyde | 10 | 10 | 10 |
| methyl dihydrojasmonate (produced by Firmenich et Cie of Geneva, Switzerland) | 100 | 100 | 100 |
| Coumarin | 20 | 20 | 20 |
| Musk Ketone | 80 | 80 | 80 |
| Isocyclocitral (10% in diethylphthalate) | 10 | 10 | 10 |
| Galbanum Oil (10% in diethylphthalate) | 6 | 6 | 6 |
| Rosemary Oil | 10 | 10 | 10 |
| Pine Needle Oil | 60 | 60 | 60 |
| Fir Balsam Absolute (10% in diethylphthalate) | 10 | 10 | 10 |
| Bergamot Oil | 60 | 60 | 60 |
| Lemon Oil | 14 | 14 | 14 |
| Benzyl Acetate | 468 | 460 | 460 |
| Linalool | 80 | 80 | 80 |
| Indol (10% in diethylphthalate) | 6 | 6 | 6 |
| Undecalactone (10% in diethylphthalate) | 12 | 12 | 12 |
| Ylang Ylang Oil | 32 | 32 | 32 |
| Alkylthio chemical I | 2 | — | — |
| Alkylthio chemical II | — | 10 | — |
| Alkylthio chemical III | — | — | 10 |

The addition of 0.2% by weight of chemical I gives increased strength to the fragrance as well as modifying the herbal character and rendering it unusual and novel. The material can be used in perfumery at from approximately 1 ppm (0.0001%) up to approximately 1%.

The weaker alcohol, chemical II, is added to the fragrance at 1% by weight. The addition of this material gives a softer effect but alters the herbal effect to an unusual and novel character. Chemical II may be used in perfumery from approximately 0.01% to 5% by weight. For special effects up to 50% may be used.

The addition of 1% of chemical III gives quite a different effect. In this case the herbal character is not altered as in the other examples, but the citrus notes are enhanced and strengthened. This chemical may be used in perfumery from approximately 0.01% to 10% by weight. For special effects up to 50% may be used.

In all cases of the above examples, the fragrance is improved by the addition of the alkylthio chemicals I, II and III and rendered more desirable and novel.

EXAMPLE XI

PREPARATION OF SOAP COMPOSITIONS 100 grams of soap chips are mixed with 1 gram of the chemical set forth in Table II below until a substantially homogeneous composition is obtained. The perfumed soap composition manifests an aroma according to the aroma set forth in Table II below:

Table II

| Compound | Aroma |
|---|---|
| 3-methylthio-4-heptanol | A sweet, green, floral, herbal, vegetative aroma with an underlying verdima nuance. |
| 3-methylthio-4-heptanone | A green, minty, herbaceous aroma with basil nuances. |
| 3-propylthio-4-heptanol | A green aroma with floral nuances. |
| 3-thioacetyl-2,6-dimethyl-4-heptanone | A grapefruit oit-like aroma. |
| 3-isobutylthio-4-heptanone | A green, spicey and peppery aroma with an underlying bergamot note. |
| 3-isobutylthio-2,6-dimethyl-4-heptanol | A green aroma containing notes of hyacinth and narcisse. |
| 3-methylthio-2,6-dimethyl-4-heptanone | A sweet, slightly floral and woody aroma with fruity and berry nuances. |
| 3-(methallylthio)-2,6-dimethyl-4-heptanone | A fruity, grapefruit, somewhat floral aroma with underlying |

EXAMPLE XII

PREPARATION OF A DETERGENT COMPOSITION

A total of 100 grams of a detergent powder (a nonionic detergent powder containing a proteolytic enzyme prepared according to Example I of Canadian Pat. No. 985,190 issued on Mar. 9, 1976) is mixed with 0.15 grams of the α-oxy(oxo) sulfides set forth in Table III below until a substantially homogeneous composition is obtained. This composition has an excellent aroma as defined in Table III below:

| Compound | Aroma |
| --- | --- |
| 3-methylthio-4-heptanol | A sweet, green, floral, herbal, vegetative aroma with an underlying verdima nuance. |
| 3-methylthio-4-heptanone | A green, minty, herbaceous aroma with basil nuances. |
| 3-propylthio-4-heptanol | A green aroma with floral nuances. |
| 3-thioacetyl-2,6-dimethyl-4-heptanone | A grapefruit oil-like aroma. |
| 3-isobutylthio-4-heptanone | A green, spicey and peppery aroma with an underlying bergamot note. |
| 3-isobutylthio-2,6-dimethyl-4-heptanol | A green aroma containing notes of hyacinth and narcisse. |
| 3-methylthio-2,6-dimethyl-4-heptanone | A sweet, slightly floral and woody aroma with fruity and berry nuances. |
| 3-(methallylthio)-2,6-dimethyl-4-heptanone | A fruity, grapefruit, somewhat floral aroma with underlying yara and neroli notes and bready, vegetative nuances. |

EXAMPLE XIII

PREPARATION OF COSMETIC POWDER COMPOSITIONS

Cosmetic powders are prepared by mixing in a ball mill 100 grams of talcum powder with 0.25 grams of each of the compounds set forth in Table IV below. Each of these powders has an excellent aroma as set forth in Table IV below.

Table IV

| Compound | Aroma |
| --- | --- |
| 3-methylthio-4-heptanol | A sweet, green, floral, herbal, vegetative aroma with an underlying verdima nuance. |
| 3-methylthio-4-heptanone | A green, minty, herbaceous aroma with basil nuances. |
| 3-propylthio-4-heptanol | A green aroma with floral nuances. |
| 3-thioacetyl-2,6-dimethyl-4-heptanone | A grapefruit oil-like aroma. |
| 3-isobutylthio-4-heptanone | A green, spicey and peppery aroma with an underlying bergamot note. |
| 3-isobutylthio-2,6-dimethyl-4-heptanol | A green aroma containing notes of hyacinth and narcisse. |
| 3-methylthio-2,6-dimethyl-4-heptanone | A sweet, slightly floral and woody aroma with fruity and berry nuances. |
| 3-(methallylthio)-2,6-dimethyl-4-heptanone | A fruity, grapefruit, somewhat floral aroma with underlying yara and neroli notes and bready, vegetative nuances. |

EXAMPLE XIV

PERFUMED LIQUID DETERGENTS

Concentrated liquid detergents with rich, pleasant aromas as set forth in Table V below are prepared containing 0.10%, 0.15% and 0.20% of an α-oxy(oxo) sulfide as set forth in Table V below. They are prepared by adding and homogeneously admixing the appropriate quantity of α-oxy(oxo) sulfide in the liquid detergent. The liquid detergents are all produced using anionic detergents containing a 50:50 mixture of sodium lauroyl sarcosinate and potassium N-methyl lauroyl taruide. The detergents all possess a pleasant fragrance as defined in the table below, the intensity increasing with greater concentration of α-oxy(oxo) sulfide of this invention.

| Compound | Aroma |
| --- | --- |
| 3-methylthio-4-heptanol | A sweet, green, floral, herbal, vegetative aroma with an underlying verdima nuance. |
| 3-methylthio-4-heptanone | A green, minty, herbaceous aroma with basil nuances. |
| 3-propylthio-4-heptanol | A green aroma with floral nuances. |
| 3-thioacetyl-2,6-dimethyl-4-heptanone | A grapefruit oil-like aroma. |
| 3-isobutylthio-4-heptanone | A green, spicey and peppery aroma with an underlying bergamot note. |
| 3-isobutylthio-2,6-dimethyl-4-heptanol | A green aroma containing notes of hyacinth and narcisse. |
| 3-methylthio-2,6-dimethyl-4-heptanone | A sweet, slightly floral and woody aroma with fruity and berry nuances. |
| 3-(methallylthio)-2,6-dimethyl-4-heptanone | A fruity, grapefruit, somewhat floral aroma with underlying yara and neroli notes and bready, vegetative nuances. |

EXAMPLE XV

An α-oxy(oxo) sulfide as set forth in Table VI below is incorporated in a cologne at a concentration of 2.5% in 85% aqueous ethanol; and into a handkerchief perfume at a concentration of 20% (in 95% aqueous ethanol). A distinct and difinite strong fragrance as set forth in Table VI below is imparted to the cologne and to the handkerchief perfume:

| Compound | Aroma |
| --- | --- |
| 3-methylthio-4-heptanol | A sweet, green, floral, herbal, vegetative aroma with an underlying verdima nuance. |
| 3-methylthio-4-heptanone | A green, minty, herbaceous aroma with basil nuances. |
| 3-propylthio-4-heptanol | A green aroma with floral nuances. |
| 3-thioacetyl-2,6-dimethyl-4-heptanone | A grapefruit oil-like aroma. |
| 3-isobutylthio-4-heptanone | A green, spicey and peppery aroma with an underlying bergamot note. |
| 3-isobutylthio-2,6-dimethyl-4-heptanol | A green aroma containing notes of hyacinth and narcisse. |
| 3-methylthio-2,6-dimethyl-4-heptanone | A sweet, slightly floral and woody aroma with fruity and berry nuances. |
| 3-(methallylthio)-2,6-dimethyl-4-heptanone | A fruity, grapefruit, somewhat floral aroma with underlying yara and neroli notes and bready, vegetative nuances. |

BRIEF DESCRIPTION OF THE DRAWINGS

FIG. 7 is the NMR spectrum for the product of Example II(C) wherein 3-methallylthio-2,6-dimethyl-4-heptanone is produced.

FIG. 8 is the infrared spectrum for the product of Example II(C) wherein 3-methallylthio-2,6-dimethyl-4-heptanone is produced.

FIG. 8(A) is the NMR spectrum for the product of Example II(D) wherein 3-thioacetyl-2,6-dimethyl-4-heptanone is produced.

FIG. 8(B) is the infrared spectrum for the product of Example II(D) wherein 3-thioacetyl-2,6-dimethyl-4-heptanone is produced.

FIG. 15 is the NMR spectrum for the product of Example V(B) wherein 3-isobutylthio-2,6-dimethyl-4-heptanol is produced.

FIG. 16 is the infrared spectrum for the product of Example V(B) wherein 3-isobutylthio-2,6-dimethyl-4-heptanol is produced.

FIG. 18 is the infrared spectrum for the product of Example VI wherein 3-methylthio-2,6-dimethyl-4-heptanone is produced.

Figure 1:
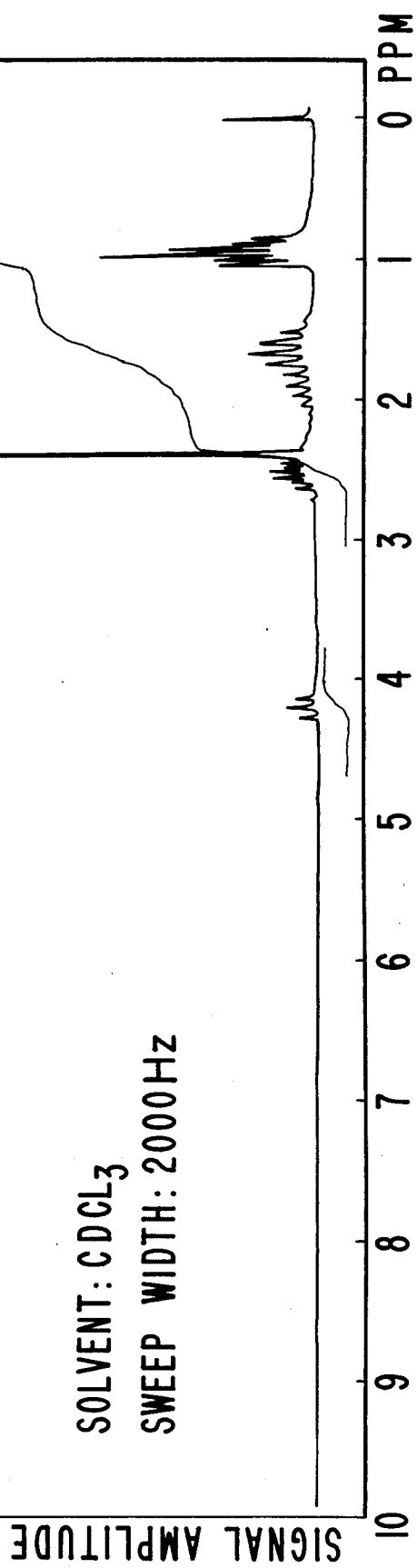
FIG. 1 is the NMR spectrum for the product of Example I(B) wherein 3-thioacetyl-4-heptanone is produced.
Figure 2:
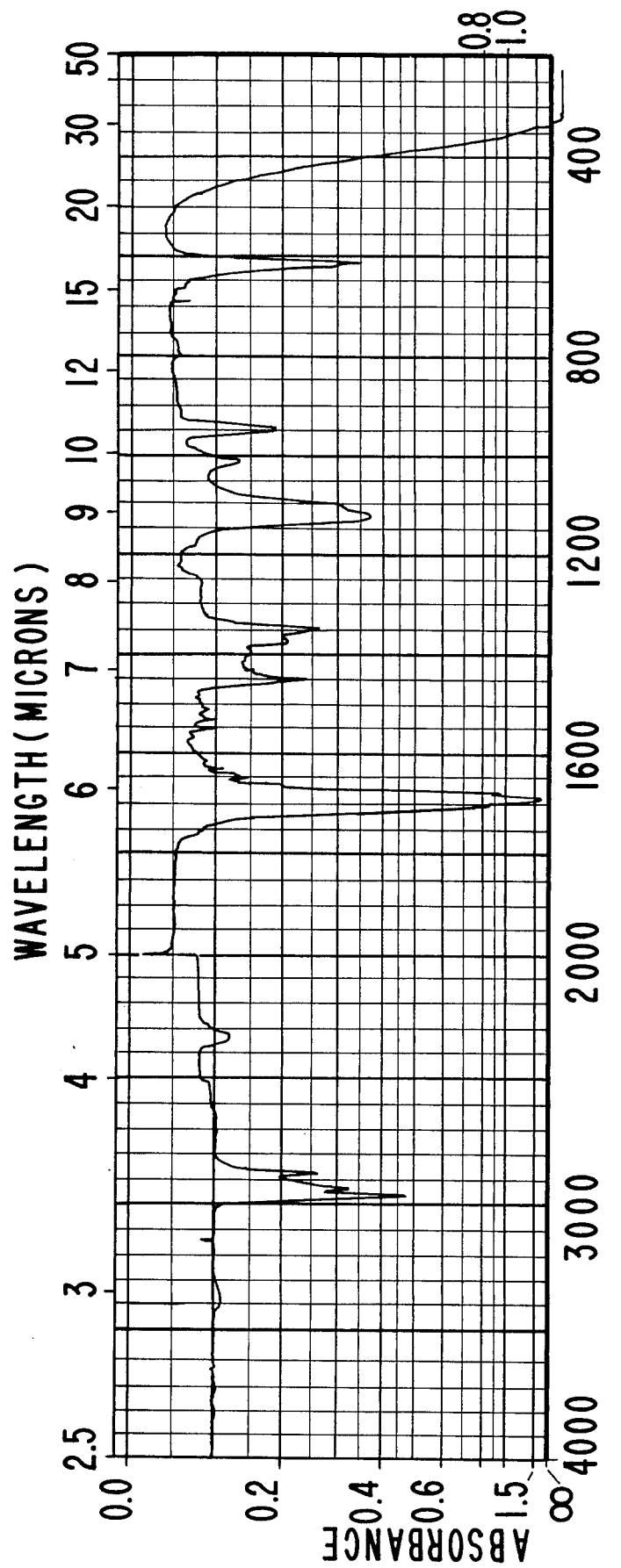
FIG. 2 is the infrared spectrum for the product of Example I(B) wherein 3-thioacetyl-4-heptanone is produced.
Figure 3:
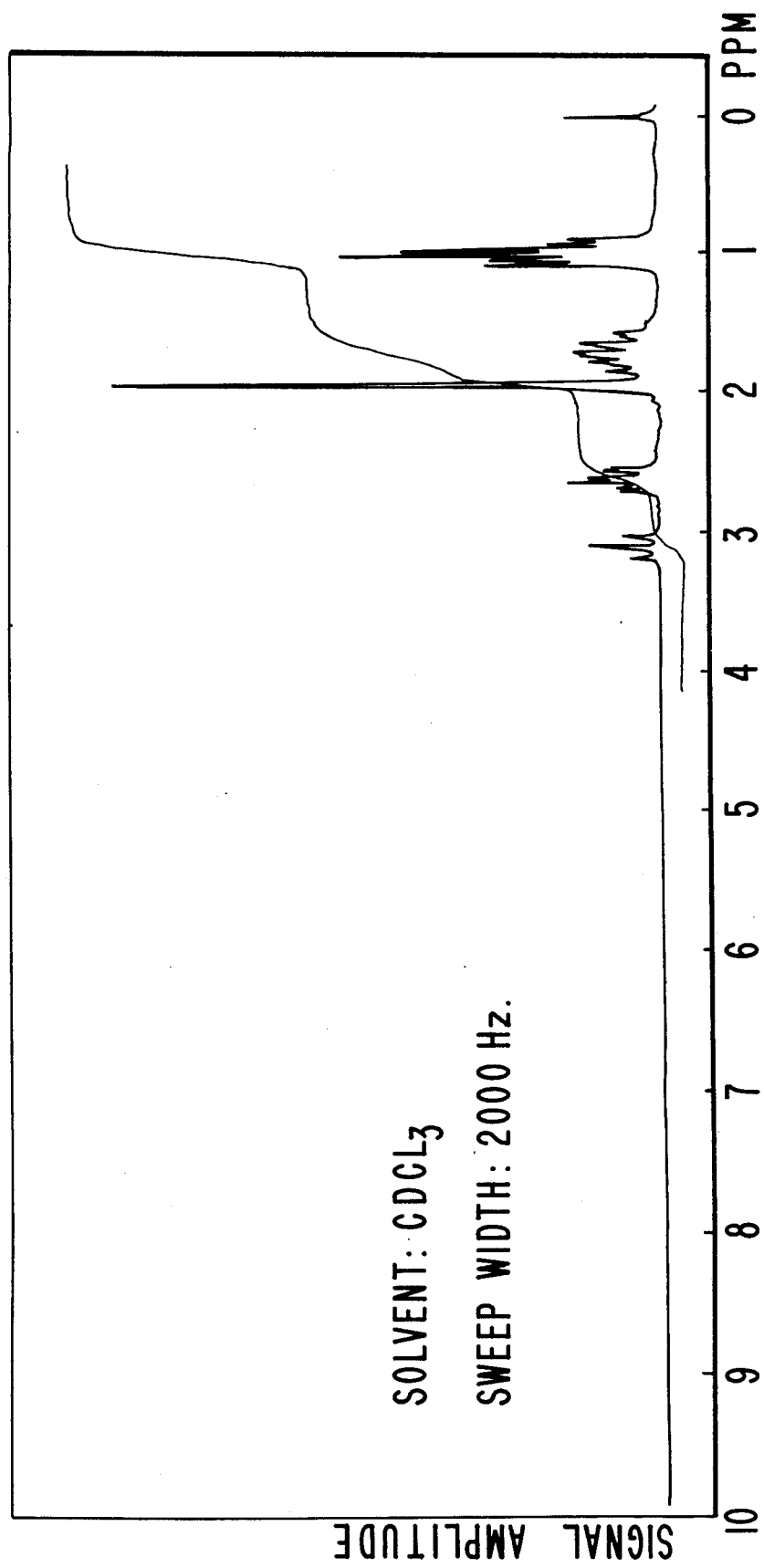
FIG. 3 is the NMR spectrum for the product of Example I (C) wherein 3-thiomethyl-4-heptanone is produced.
Figure 4:
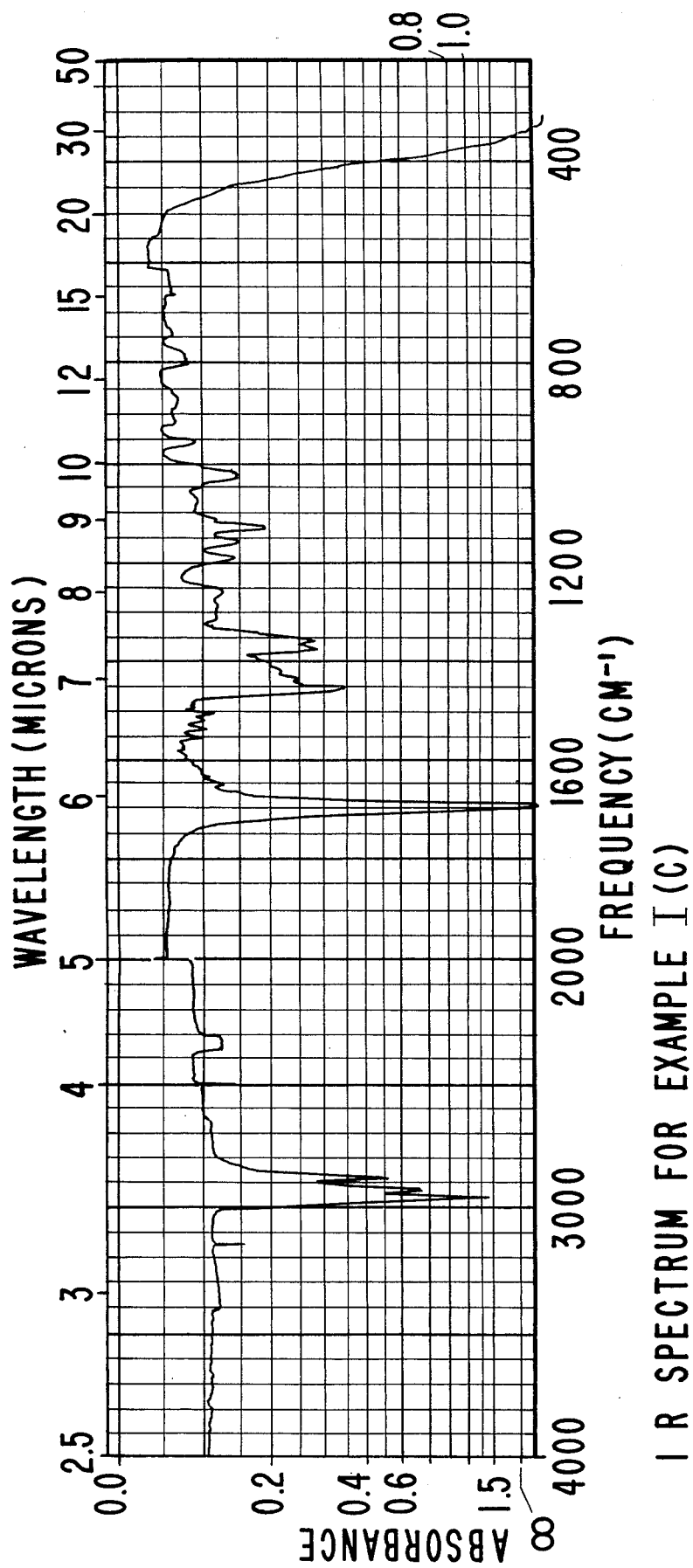
FIG. 4 is the infrared spectrum for the product of Example I(C) wherein 3-thiomethyl-4-heptanone is produced.
Figure 5:
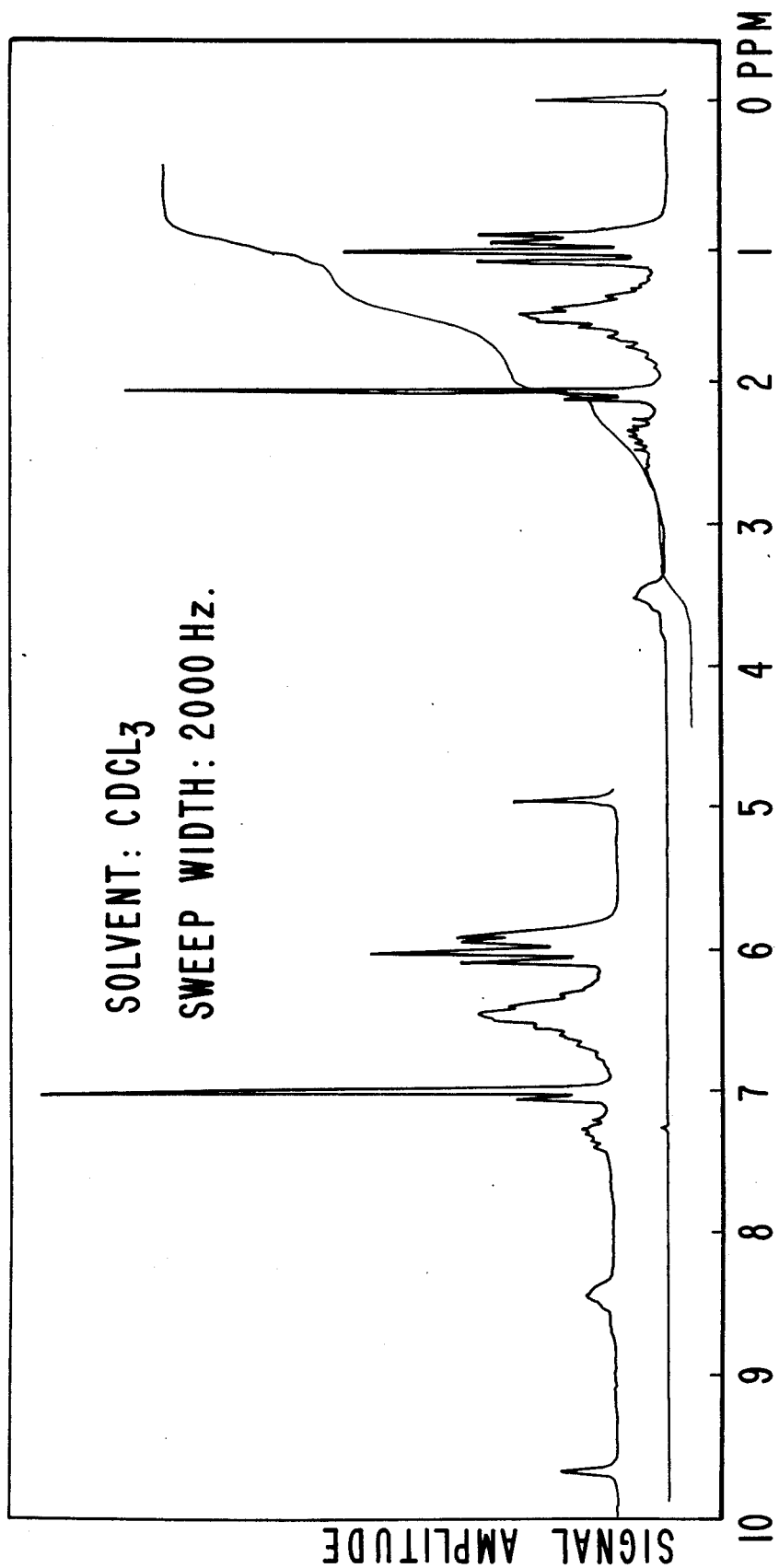
FIG. 5 is the NMR spectrum for the product of Example I(D) wherein 3-thiomethyl-4-heptanol is produced.
Figure 6:
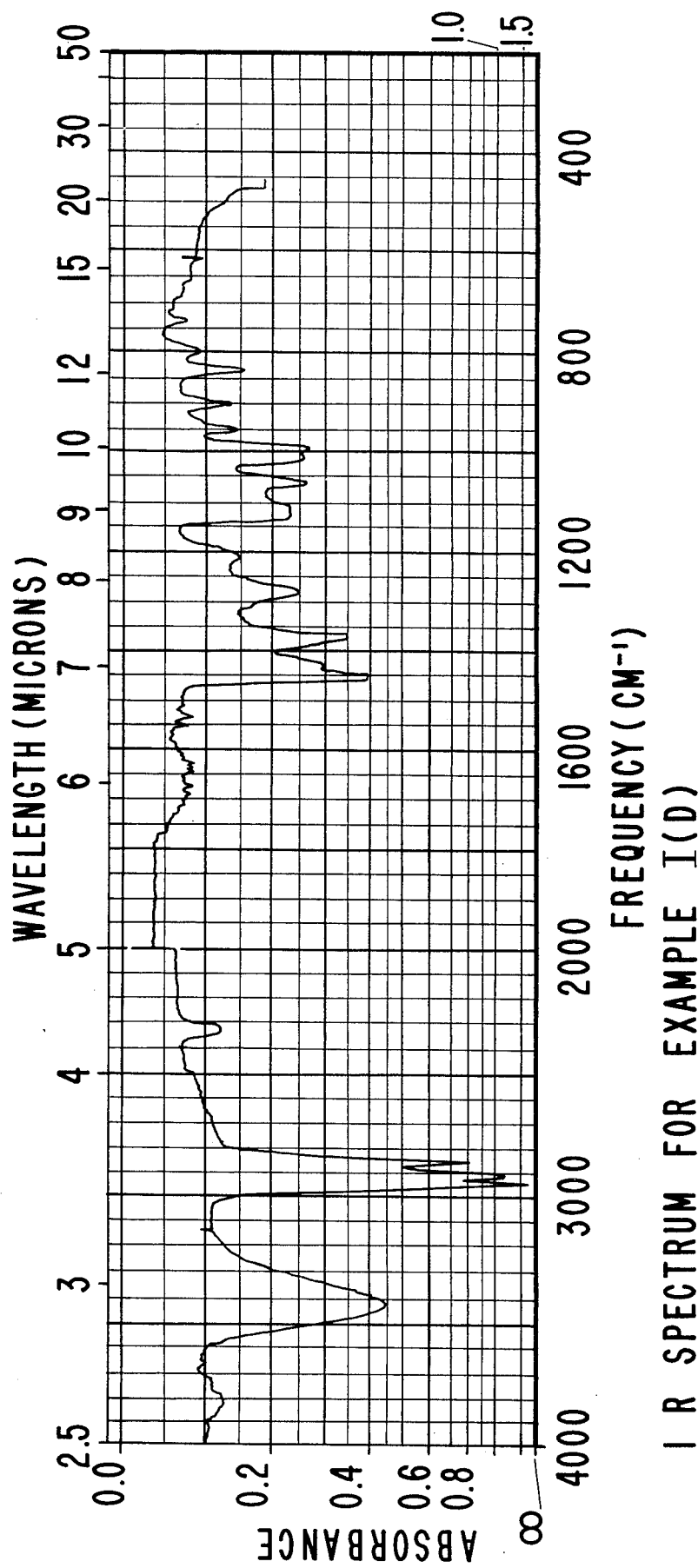
FIG. 6 is the infrared spectrum for the product of Example I(D) wherein 3-thiomethyl-4-heptanol is produced.
Figure 9:
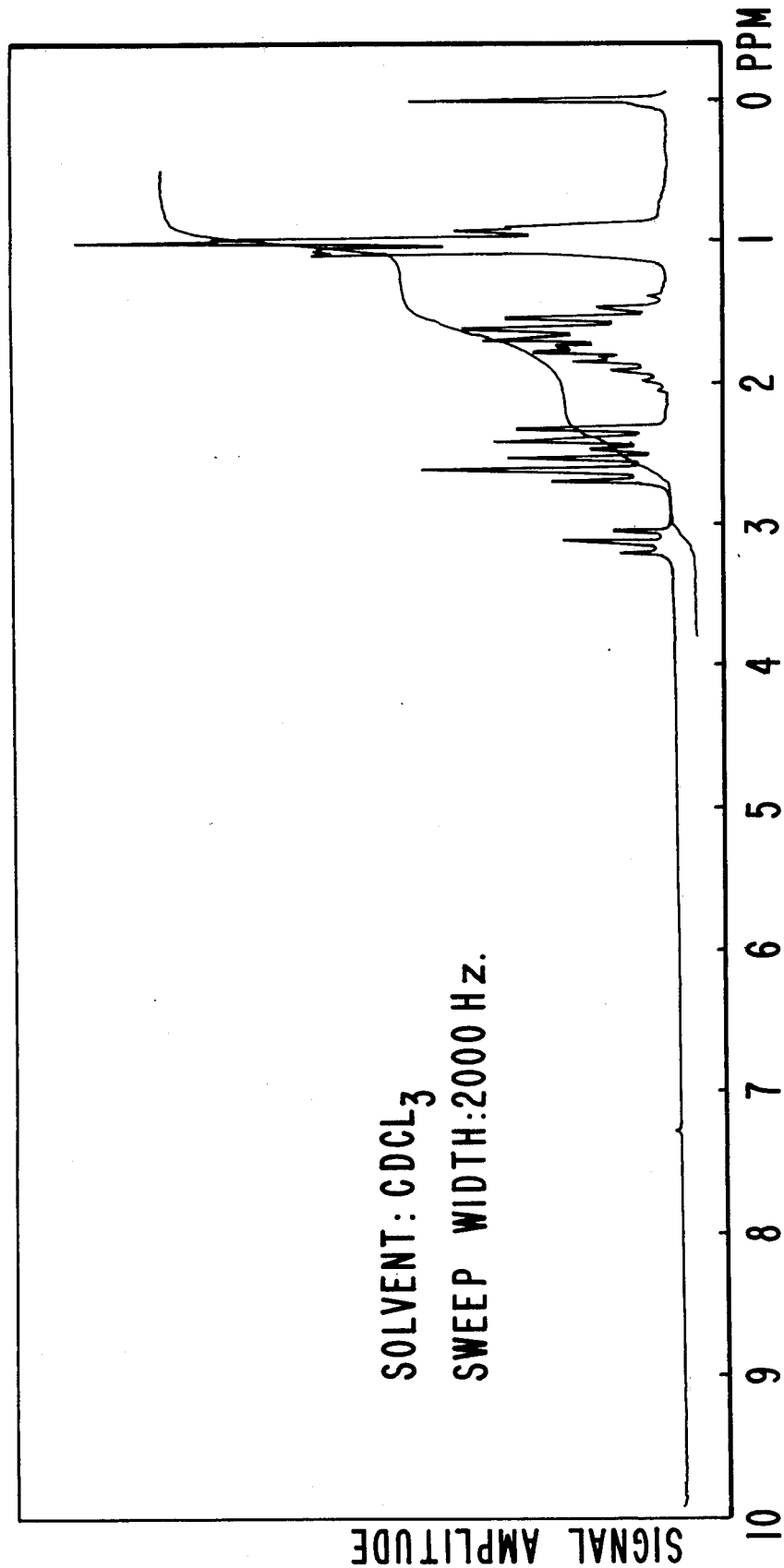
FIG. 9 is the NMR spectrum for the product of Example III(A) wherein 3-propylthio-4-heptanone is produced.
Figure 10:
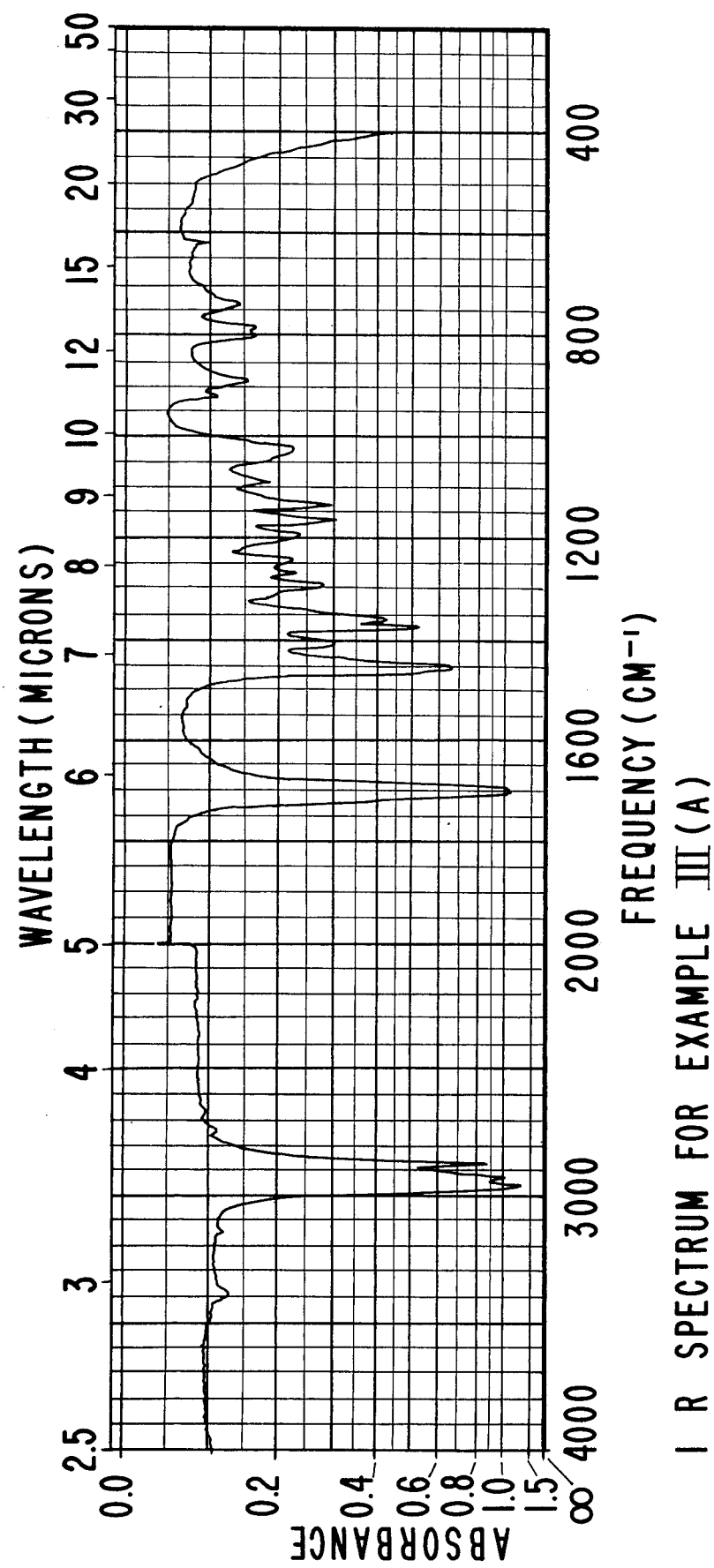
FIG. 10 is the infrared spectrum for the product of Example III(A) wherein 3-propylthio-4-heptanone is produced.
Figure 11:
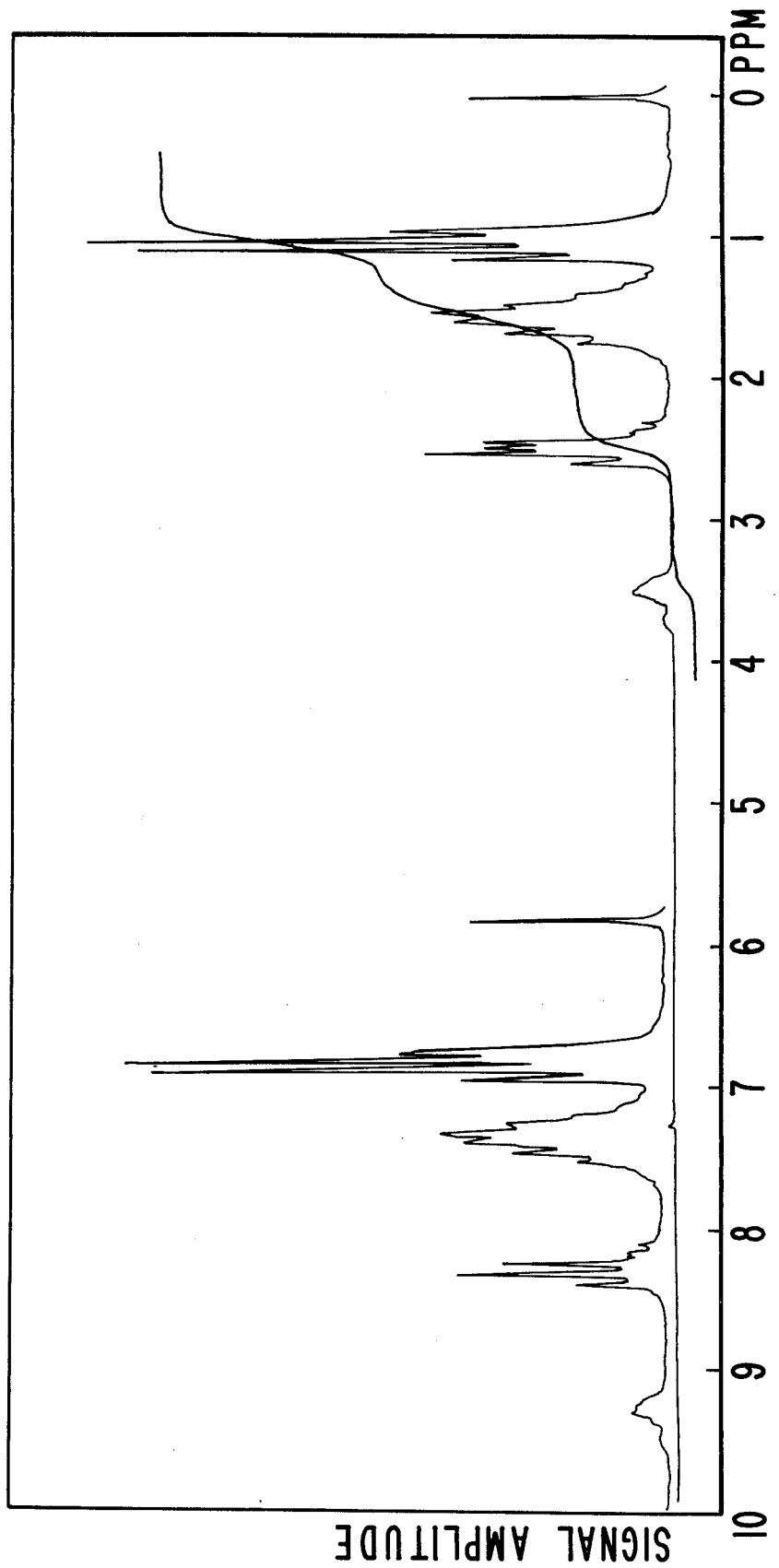
FIG. 11 is the NMR spectrum for the product of Example III (B) wherein 3-propylthio-4-heptanol is produced.
Figure 12:
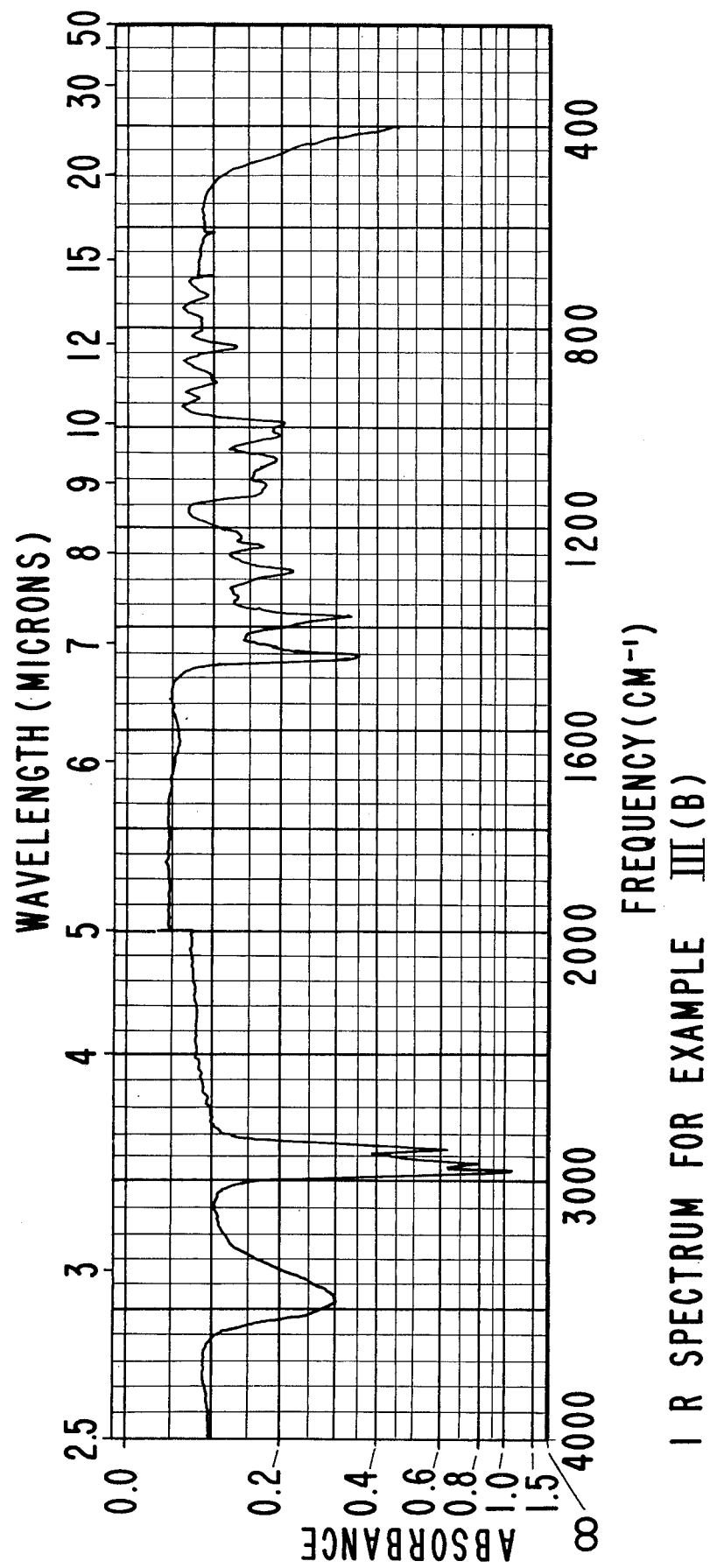
FIG. 12 is the infrared spectrum for the product of Example III(B) wherein 3-propylthio-4-heptanol is produced.
Figure 13:
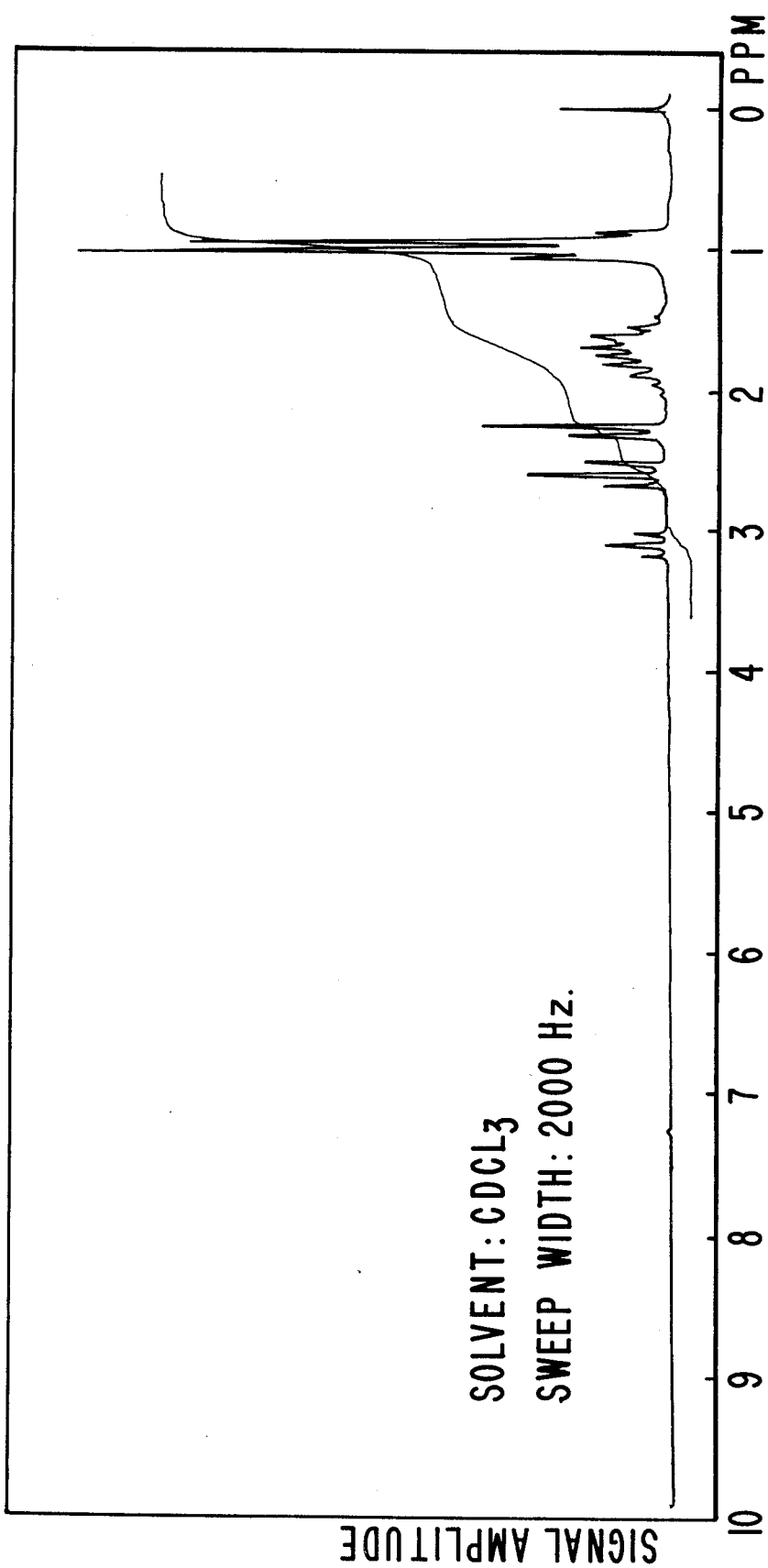
FIG. 13 is the NMR spectrum for the product of Example IV wherein 3-isobutylthio-4-heptanone is produced.
Figure 14:
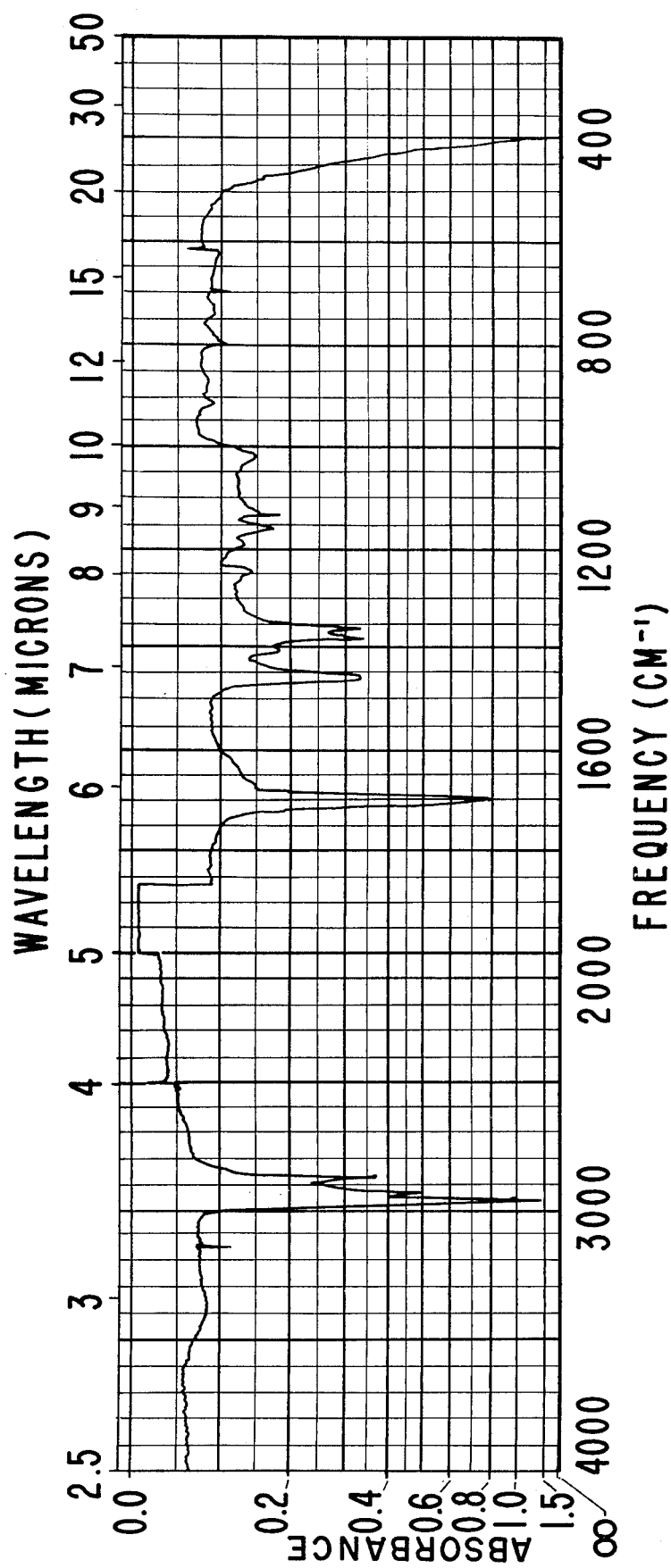
FIG. 14 is the infrared spectrum for the product of Example IV wherein 3-isobutylthio-4-heptanone is produced.
Figure 14A:
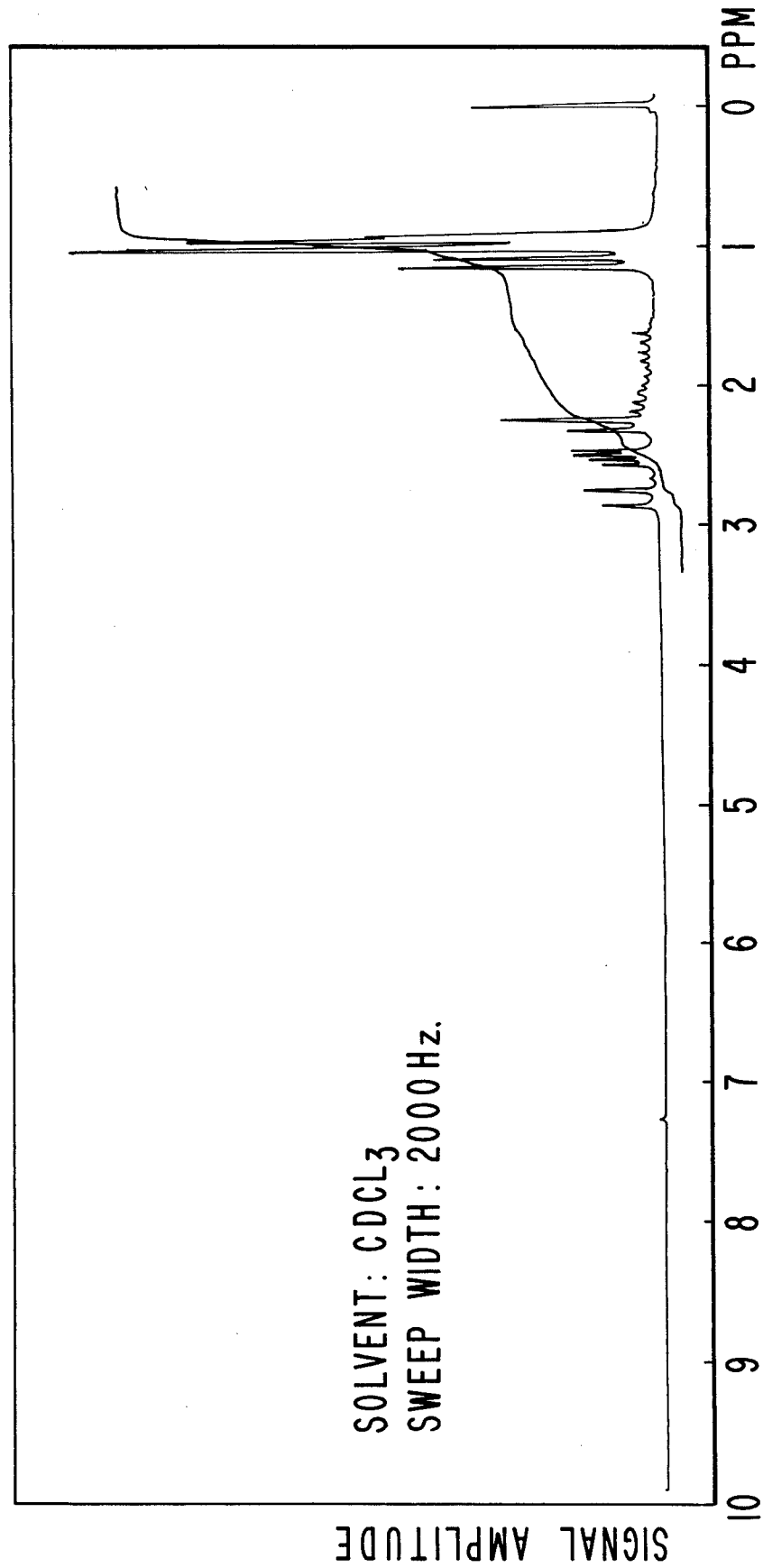
FIG. 14(A) is the NMR spectrum for the product of Example V(A) wherein 3-isobutylthio-2,6-dimethyl-4-heptanone is produced.
Figure 14B:
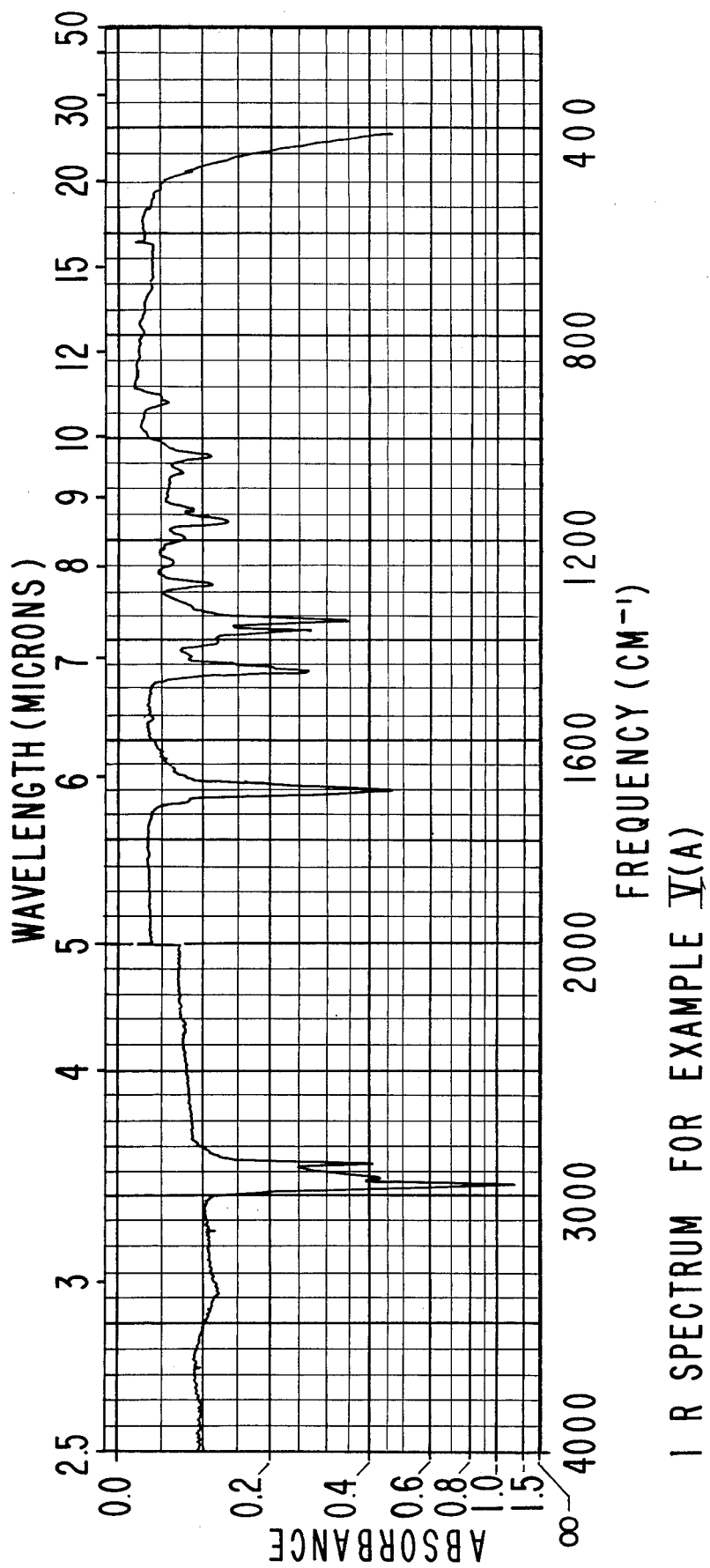
FIG. 14(B) is the infrared spectrum for the product of Example V(A) wherein 3-isobutylthio-2,6-dimethyl-4-heptanone is produced.
Figure 17:
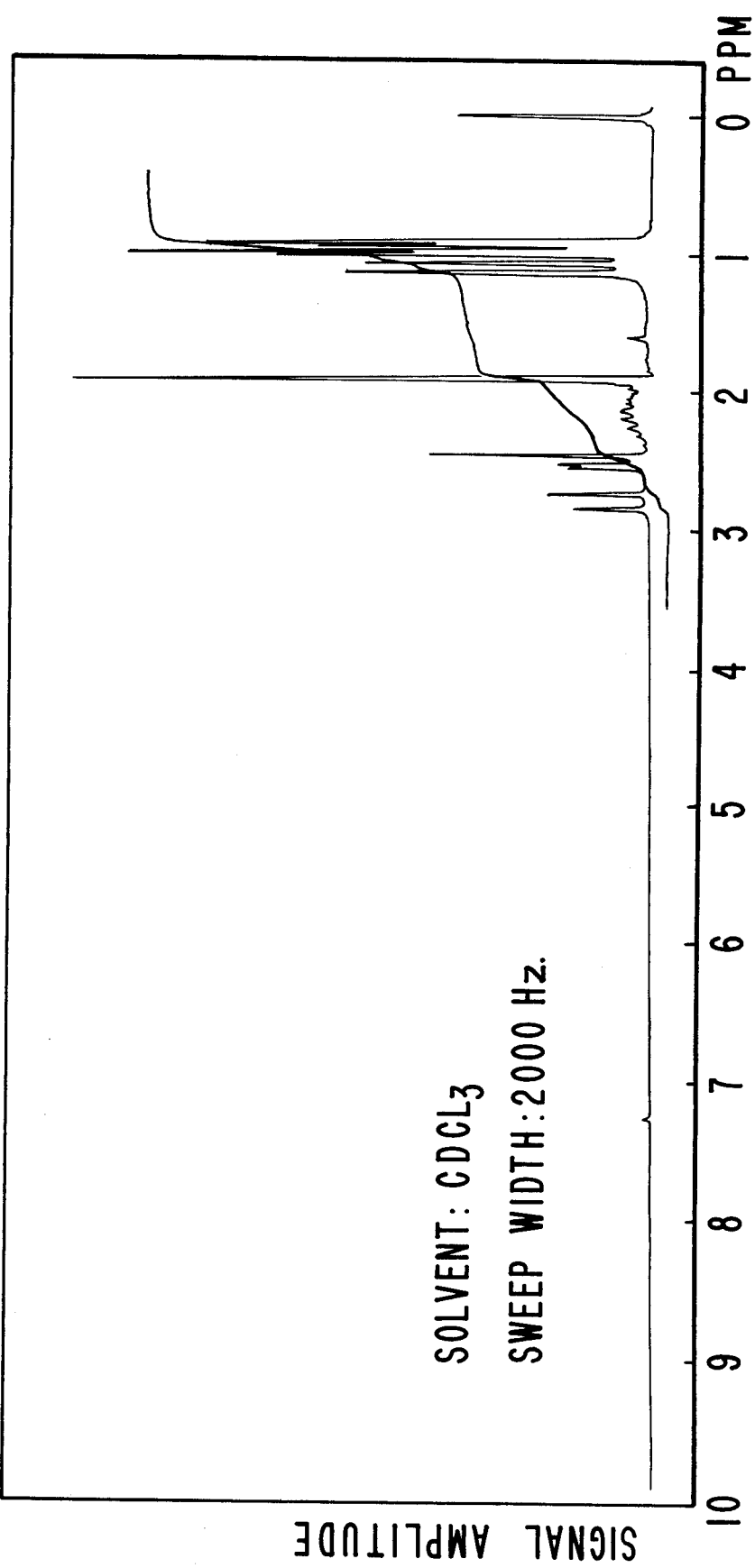
FIG. 17 is the NMR spectrum for the product of Example VI wherein 3-methylthio-2,6-dimethyl-4-heptanone is produced.

What is claimed is:

1. A perfume comprising a carrier and a compound having the structure:

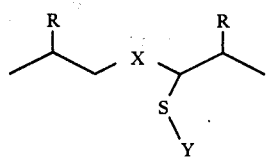

wherein R is one of hydrogen or methyl, X is a moiety having the structure:

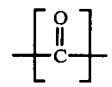

and Y is selected from the group consisting of methyl, methallyl, having the structure:

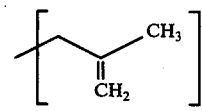

1-propyl, 2-methyl-1-propyl and acetyl.

2. A perfume composition comprising a perfuming quantity of at least one of the compounds defined according to claim 1, and at least one adjuvant selected from the group consisting of natural perfume oils, synthetic perfume oils, alcohols, aldehydes, ketones, nitriles, esters and lactones.

3. A process for producing a perfumed composition comprising the step of intimately admixing at least one compound defined according to claim 1 and at least one material selected from the group consisting of natural perfume oil, synthetic perfume oils, alcohols, aldehydes, ketones, nitriles, esters and lactones.

4. A cologne composition comprising at least one compound defined according to claim 1, ethanol and water.

5. The composition of claim 1 wherein, in the compound, R is methyl and Y is methallyl.

6. The composition of claim 1 wherein, in the compound, R is hydrogen and Y is methyl.

7. A perfume composition comprising a perfuming quantity of the compound defined according to claim 5, and at least one adjuvant selected from the group consisting of natural perfume oils, synthetic perfume oils, alcohols, aldehydes, ketones, nitriles, esters and lactones.

8. A process for producing a perfumed composition comprising the step of intimately admixing the compound defined according to claim 5 and at least one material selected from the group consisting of natural perfume oils, synthetic perfume oils, alcohols, aldehydes, ketones, nitriles, esters and lactones.

9. A cologne composition comprising the compound defined according to claim 5, ethanol and water.

10. A perfume composition comprising a perfuming quantity of the compound defined according to claim 6, and at least one adjuvant selected from the group consisting of natural perfume oils, synthetic perfume oils, alcohols, aldehydes, ketones, nitriles, esters and lactones.

11. A process for producing a perfumed composition comprising the step of intimately admixing the compound defined according to claim 6 and at least one material selected from the group consisting of natural perfume oils, synthetic perfume oils, alcohols, aldehydes, ketones, nitriles, esters and lactones.

12. A cologne composition comprising the compound defined according to claim 6, ethanol and water.

* * * * *